United States Patent [19]

Pitteloud

[11] Patent Number: 5,710,198

[45] Date of Patent: Jan. 20, 1998

[54] CYCLIC DIPHENYLACETONITRILES AS STABILIZERS

[75] Inventor: Rita Pitteloud, Praroman, Switzerland

[73] Assignee: Ciba Specialty Chemicals Corporation, Tarrytown, N.Y.

[21] Appl. No.: 662,108

[22] Filed: Jun. 14, 1996

Related U.S. Application Data

[63] Continuation of Ser. No. 180,399, Jan. 11, 1994, abandoned.

[30] Foreign Application Priority Data

Jan. 18, 1993 [CH] Switzerland ............... 129/93

[51] Int. Cl.$^6$ ............... C08K 5/15; C08K 5/45
[52] U.S. Cl. ............... 524/110; 524/84; 252/406; 252/407
[58] Field of Search ............... 252/400.1, 406, 252/407; 524/110, 82

[56] References Cited

U.S. PATENT DOCUMENTS

| | | | |
|---|---|---|---|
| 2,956,063 | 10/1960 | Baltzley et al. | 260/335 |
| 3,042,674 | 7/1962 | Faust et al. | 260/251 |
| 3,452,076 | 6/1969 | Mahr et al. | 260/466 |
| 3,641,038 | 2/1972 | Davis et al. | 260/289 |
| 4,105,665 | 8/1978 | Harnisch | 524/110 |
| 4,325,863 | 4/1982 | Hinsken et al. | 624/111 |
| 4,338,244 | 7/1982 | Hinsken et al. | 524/109 |
| 5,175,312 | 12/1992 | Dubs et al. | 549/307 |
| 5,302,497 | 4/1994 | Berner et al. | 430/512 |
| 5,306,829 | 4/1994 | Berner et al. | 549/223 |

FOREIGN PATENT DOCUMENTS

| | | | |
|---|---|---|---|
| 4202276 | 8/1992 | Germany. | |
| 60088087 | of 1985 | Japan. | |
| 1229087 | 9/1989 | Japan | 524/110 |

OTHER PUBLICATIONS

Deru. Abst. 84–157885.
Kobayashi et al. J. Chem. Soc. Chem. Commun. 1992, 780.
M.A. Davis et al. J. Med. Chem. vol. 7, 88 (1964).
M.A. Davis et al. Cana. Jour. of Chem. vol. 47 (15), 2827 (1969).
J. Org. Chem. vol. 51, 1986, 717–723. Pillai et al.
C.C. Price et al., J. Amer. Chem. Soc. vol. 85, 2278 (1963).
Berti et al., Gazz. Chim. Ital. vol. 87, 293 (1957).
V. Mychajlysyyen et al., Coll. Czech. Chem. Comm. vol. 24, 3955 (1959).
Chem. Abst. 103, 124 501d.
Chem. Abst. 103, 124491 a.
A. Kaufmann et al., Ber. 42, 1999 (1909).
V. Valenta et al. Coll. Czech Chem. Comm. 53 (4), 860 (1988).
J. Org. Chem. vol. 45, 2468–2473 (1980) Hari et al.
M.N. Romanelli et al. Il Farmacee vol. 46 (10) 1121 (1991).

*Primary Examiner*—Kriellion S. Morgan
*Attorney, Agent, or Firm*—Luther A.R. Hall; Michele A. Kovaleski; Victoria M. Malia

[57] ABSTRACT

Compounds of the formula I

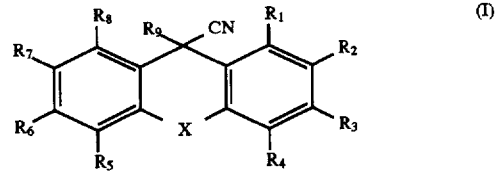

(I)

in which the general symbols are as defined in claim 1, as stabilizers for organic materials against thermal, oxidative or light-induced degradation are described.

16 Claims, No Drawings

CYCLIC DIPHENYLACETONITRILES AS STABILIZERS

This application is a continuation of application Ser. No. 08/180,399, filed Jan. 11, 1994 now abandoned.

The present invention relates to compositions comprising an organic material, preferably a polymer, and cyclic diphenylacetonitriles as stabilizers, the use thereof for stabilizing organic materials against oxidative, thermal or light-induced degradation and novel cyclic diphenylacetonitriles.

Individual cyclic diphenylacetonitriles are known in the literature and have been described, for example, by M. N. Romanelli et al, II Farmaco 46 (10), 1121 (1991); M. Hori et at, J. Org. Chem. 45 (12), 2468 (1980); V. Valenta et at, Coil. Czech. Chem. Comm. 53 (4), 860 (1988); M. A. Davis et at, J. Meal. Chem. 7, 88 (1964); and A. Kaufmann et al, Ber. Dt. Chem. Ges. 42, 1999 (1909); and in U.S. Pat. Nos. 3,452,076 or 2,956,063. In no publication are these compounds used as stabilizers for organic materials.

The use of some dibenzopyrans as stabilizers for organic materials has been described, for example, in JP-A-60 084 383 and JP-A-60 088 087.

It has now been found that a selected group of cyclic diphenylacetonitriles is particularly suitable as stabilizers for organic materials which are sensitive to oxidative, thermal or light-induced degradation.

The present invention therefore relates to compositions comprising a) an organic material subjected to oxidative, thermal or light-induced degradation and b) at least one compound of the formula I

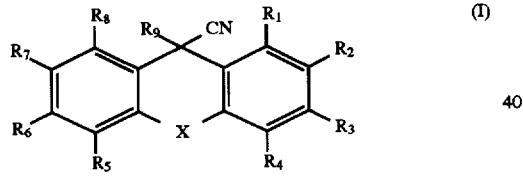

in which $R_1$, $R_2$, $R_3$, $R_4$, $R_5$, $R_6$, $R_7$ and $R_8$ independently of one another are hydrogen, halogen, $C_1$–$C_{25}$alkyl or $C_2$–$C_{25}$alkyl which is interrupted by oxygen, sulfur or

$C_5$–$C_8$cycloalkyl which is unsubstituted or substituted by $C_1$–$C_4$alkyl; phenyl which is unsubstituted or substituted by $C_1$–$C_4$alkyl; $C_7$–$C_9$phenylalkyl, hydroxyl, $C_1$–$C_8$alkoxy or $C_3$–$C_{18}$-alkoxy which is interrupted by oxygen, sulfur or

mercapto, $C_1$–$C_{18}$alkylthio or $C_3$–$C_{18}$alkylthio which is interrupted by oxygen, sulfur or

$C_1$–$C_{25}$alkanoyloxy or $C_3$–$C_{25}$alkanoyloxy which is interrupted by oxygen, sulfur or

$C_3$–$C_{25}$alkenoyloxy, benzoyloxy or benzoyloxy which is substituted by $C_1$–$C_{12}$alkyl; nitro, cyano, —(CH$_2$)$_m$COR$_{11}$ or

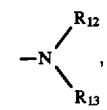

and furthermore the radicals $R_1$ and $R_2$, $R_2$ and $R_3$, $R_3$ and

R4, $R_5$ and $R_6$, $R_6$ and $R_7$ or $R_7$ and $R_s$, together with the carbon atoms to which they are bonded, form a benzo ring, or the same pairs of radicals together are —O(CH$_2$)$_n$O—, with the condition that at least one of the radicals $R_1$, $R_2$, $R_3$ or R4 and at least one of the radicals $R_5$, $R_6$, $R_7$ or $R_8$ is hydrogen, $R_1$ is additionally a radical of the formula II, $R_2$ is additionally a radical of the formula III, $R_3$ is additionally a radical of the formula IV and $R_4$ is additionally a radical of the formula V, and at the same time only one radical of the formula II, III, IV or V occurs in the compound of the formula I.

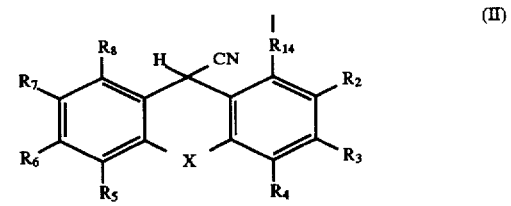

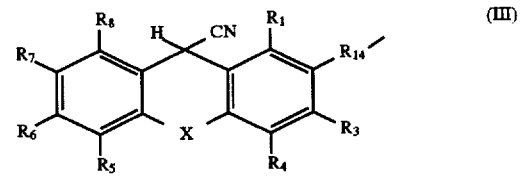

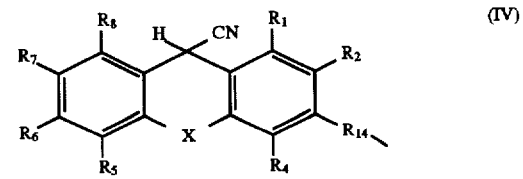

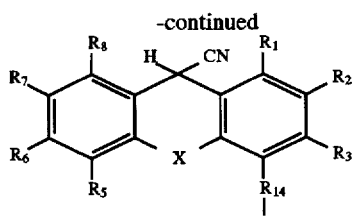

(V)

$R_9$ is hydrogen or a radical of the formula VI

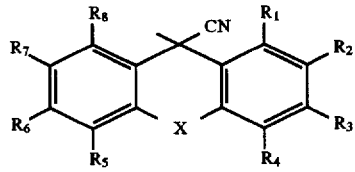

(VI)

in which $R_1$, $R_2$, $R_3$ and $R_4$ are not a radical of the formula II, III, IV or V, $R_{10}$ is hydrogen or $C_1$–$C_8$alkyl, $R_{11}$ is hydroxyl, $C_1$–$C_{18}$alkoxy or

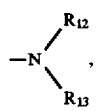

$R_{12}$ and $R_{13}$ independently of one another are hydrogen or $C_1$–$C_8$alkyl, $R_{14}$ is a direct bond, $C_1$–$C_{18}$alkylene or $C_2$–$C_{18}$alkylene which is interrupted by oxygen, sulfur or

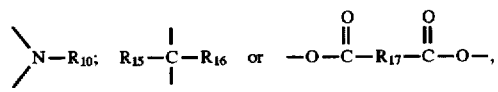

$R_{15}$ and $R_{16}$ independently of one another are hydrogen, $CF_3$, $C_1$–$C_{12}$alkyl or phenyl, or $R_{15}$ and $R_{16}$, together with the C atom to which they are bonded, form a $C_5$–$C_8$cycloalkylidene ring which is unsubstituted or substituted by 1 to 3 $C_1$–$C_4$alkyl groups, $R_{17}$ is a direct bond, $C_1$–$C_{18}$alkylene or $C_2$–$C_{18}$alkylene which is interrupted by oxygen, sulfur or

$C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, phenylene which is unsubstituted or substituted by $C_1$–$C_4$alkyl,

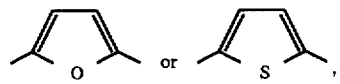

$R_8$ is hydrogen, $C_1$–$C_{25}$alkyl or $C_2$–$C_{25}$alkyl which is interrupted by oxygen, sulfur or

$C_5$–$C_8$cycloalkyl which is unsubstituted or substituted by $C_1$–$C_4$alkyl; phenyl which is unsubstituted or substituted by $C_1$–$C_4$alkyl; $C_7$–$C_9$phenylalkyl, hydroxyl, $C_1$–$C_{18}$alkoxy or $C_3$–$C_{18}$alkoxy which is interrupted by oxygen, sulfur or

$C_1$–$C_{25}$alkanoyl, $C_3$–$C_{25}$alkanoyl which is interrupted by oxygen, sulfur or

$C_3$–$C_{25}$alkenoyl, benzoyl or benzoyl which is substituted by $C_1$–$C_{12}$alkyl; cyano, —$(CH_2)_m COR_{11}$ or

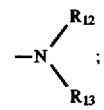

$R_{19}$ is $C_1$–$C_{25}$alkyl, $C_7$–$C_9$phenylalkyl or —$CH_2CH_2OH$,

X is a direct bond, oxygen, sulfur, —SO—, —$SO_2$—, —$CH_2$—, —$CH_2CH_2$—, —CH=CH—,

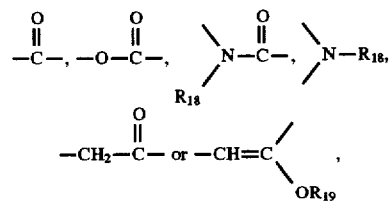

m is 0, 1 or 2 and n is 1 or 2.

Halogen is, for example, chlorine, bromine or iodine. Chlorine is preferred.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. A preferred definition of $R_2$ is $C_1$–$C_8$alkyl, in particular $C_1$–$C_2$alkyl. A particularly preferred definition of $R_4$ is $C_1$–$C_8$alkyl, in particular $C_1$–$C_4$alkyl.

$C_2$-$C_{25}$Alkyl which is interrupted by oxygen, sulfur or

is, for example, $CH_3$—O—$CH_2$—, $CH_3$—S—$CH_2$—, $CH_3$—NH—$CH_2$—, $CH_3$—N($CH_3$)—$CH_2$—, $CH_3$—O—$CH_2CH_2$—O—$CH_2$—, $CH_3$—(O—$CH_2CH_2$—$)_2$O—$CH_2$—, $CH_3$—(O—$CH_2CH_2$—$)_3$O—$CH_2$— or $CH_3$—(O—$CH_2CH_2$—$)_4$O—$CH_2$—. $C_5$-$C_8$Cycloalkyl, in particular $C_5$-$C_6$cycloalkyl, which is unsubstituted or substituted by $C_1$-$C_4$alkyl is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Cyclohexyl and tert-butylcyclohexyl are preferred.

Phenyl which is substituted by $C_1$-$C_4$alkyl and preferably contains 1 to 3, in particular 1 or 2, alkyl groups is, for example, o-, m- or p-methylphenyl, 2,3-dimethylphenyl, 2,4-di-methylphenyl, 2,5-dimethylphenyl, 2,6-dimethylphenyl, 3,4-dimethylphenyl, 3,5-di-methylphenyl, 2-methyl-6-ethylphenyl, 4-tert-butylphenyl, 2-ethylphenyl or 2,6-diethyl-phenyl.

$C_7$-$C_9$Phenylalkyl is, for example, benzyl, α-methylbenzyl, α,α-dimethylbenzyl or 2-phenylethyl.

Alkoxy having up to 18 carbon atoms is a branched or unbranched radical, for example methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. A preferred definition of $R_2$ is $C_1$-$C_6$alkoxy, in particular $C_1$-$C_3$alkoxy. A preferred definition of $R_{11}$ is $C_1C_{12}$alkoxy.

$C_3$-$C_{18}$Alkoxy which is interrupted by oxygen, sulfur or

is, for example, $CH_3$—O—$CH_2CH_2$O—, $CH_3$—S—$CH_2CH_2$O—, $CH_3$—NH—$CH_2CH_2$O—, $CH_3$—N($CH_3$)—$CH_2CH_2$O—, $CH_3$—O—$CH_2CH_2$—O—$CH_2CH_2$O—, $CH_3$—(O—$CH_2CH_2$—$)_2$O—$CH_2CH_2$O—, $CH_3$—(O—$CH_2CH_2$—$)_3$O—$CH_2CH_2$O— or $CH_3$—(O—$CH_2CH_2$—$)_4$O—$CH_2CH_2$O—.

Alkylthio having up to 18 carbon atoms is a branched or unbranched radical, for example methylthio, ethylthio, propylthio, isopropylthio, n-butylthio, isobutylthio, pentylthio, iso-pentylthio, hexylthio, heptylthio, octylthio, decylthio, tetradecylthio, hexadecylthio or octadecylthio. Alkylthio having 1 to 12, in particular 1 to 8, for example 1 to 6, carbon atoms is preferred.

$C_3$-$C_8$Alkylthio which is interrupted by oxygen, sulfur or

is, for example, $CH_3$—O—$CH_2CH_2$S—, $CH_3$—S—$CH_2CH_2$S—, $CH_3$—NH—$CH_2CH_2$S—, $CH_3$—N($CH_3$)—$CH_2CH_2$S—, $CH_3$—O—$CH_2CH_2$—O—$CH_2CH_2$S—, $CH_3$—(O—$CH_2CH_2$—$)_2$O—$CH_2CH_2$S—, $CH_3$—(O—$CH_2CH_2$—$)_3$O—$CH_2CH_2$S— or $CH_3$—(O—$CH_2CH_2$—$)_4$O—$CH_2CH_2$S—.

Alkanoyloxy having up to 25 carbon atoms is a branched or unbranched radical, for example formyloxy, acetyloxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, eicosanoyloxy or docosanoyloxy. Alkanoyloxy having 2 to 18, in particular 2 to 12, carbon atoms is preferred.

$C_3$-$C_{25}$Alkanoyloxy which is interrupted by oxygen, sulfur or

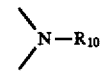

is, for example, $CH_3$—O—$CH_2$COO—, $CH_3$—S—$CH_2$COO—, $CH_3$—NH—$CH_2$COO—, $CH_3$—N($CH_3$)—$CH_2$COO—, $CH_3$—O—$CH_2CH_2$—O—$CH_2$COO—, $CH_3$—(O—$CH_2CH_2$—$)_2$O—$CH_2$COO—, $CH_3$—(O—$CH_2CH_2$—$)_3$O—$CH_2$COO— or $CH_3$—(O—$CH_2CH_2$—$)_4$O—$CH_2$COO—.

Alkenoyloxy having 3 to 25 carbon atoms is a branched or unbranched radical, for example propenoyloxy, 2-butenoyloxy, 3-butenoyloxy, isobutenoyloxy, n-2,4-pentadienoyloxy, 3-methyl-2-butenoyloxy, n-2-octenoyloxy, n-2-dodecenoyloxy, iso-dodecenoyloxy, oleoyloxy, n-2-octadecenoyloxy or n-4-octadecenoyloxy. Alkenoyloxy having 3 to 18, in particular 3 to 12, for example 3 to 6, above all 3 to 4, carbon atoms is preferred.

Benzoyloxy which is substituted by $C_1$-$C_{12}$alkyl and preferably carries 1 to 3, in particular 1 or 2, alkyl groups is, for example, o-, m- or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4-tert-butyl-benzoyloxy, 2-ethylbenzoyloxy, 2,4,6-trimethylbenzoyloxy, 2,6-dimethyl-4-tert-butylbenzoyloxy or 3,5-di-tert-butylbenzoyloxy. Preferred substituents are $C_1$-$C_8$alkyl, in particular $C_1$-$C_4$alkyl.

$C_1$-$C_{18}$Alkylene is a branched or unbranched radical, for example methylene, ethylene, propylene, trimethylene; tetramethylene, pentamethylene, hexamethylene, heptamethylene, octamethylene, decamethylene, dodecamethylene or octadecamethylene. $C_1$-$C_{12}$Alkylene, in particular $C_1$-$C_8$ alkylene, is preferred.

$C_2$-$C_{18}$Alkylene which is interrupted by oxygen, sulfur or

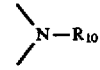

is, for example, —$CH_2$—O—$CH_2$—, —$CH_2$—S—$CH_2$—, —$CH_2$—NH—$CH_2$—, —$CH_2$—N($CH_3$)—$CH_2$—, —$CH_2$—O—$CH_2CH_2$—O—$CH_2$—, —$CH_2$—(O—$CH_2CH_2$—$)_2$O—$CH_2$—, —$CH_2$—(O—$CH_2CH_2$—$)_3$O—$CH_2$—, —$CH_2$—(O—$CH_2CH_2$—$)_4$O—$CH_2$— or —$CH_2CH_2$—S—$CH_2CH_2$—.

A $C_5$-$C_8$cycloalkylidene ring which is unsubstituted or substituted by $C_1$-$C_4$alkyl and preferably contains 1 to 3, in particular 1 or 2, branched or unbranched alkyl group radicals is, for example, cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Cyclohexylidene and tert-butylcyclohexylidene are preferred.

$C_2$–$C_{18}$Alkenylene is, for example, vinylene, methylvinylene, octenylethylene or dodecenylethylene. $C_2$–$C_8$Alkenylene is preferred.

Alkylidene having 2 to 20 carbon atoms is, for example, ethylidene, propylidene, butylidene, pentylidene, 4-methylpentylidene, heptylidene, nonylidene, tridecylidene, nonadecylidene, 1-methylethylidene, 1-ethylpropylidene or 1-ethylpentylidene. $C_2$–$C_8$Alkylidene is preferred.

Phenylalkylidene having 7 to 20 carbon atoms is, for example, benzylidene, 2-phenyl-ethylidene or 1-phenyl-2-hexylidene. $C_7$–$C_9$Phenylalkylidene is preferred.

$C_5$–$C_8$Cycloalkylene is a saturated hydrocarbon group having two free valencies and at least one ring unit and is, for example, cyclopentylene, cyclohexylene, cycloheptylene or cyclooctylene. Cyclohexylene is preferred.

$C_7$–$C_8$Bicycloalkylene is, for example, bicycloheptylene or bicyclooctylene.

Phenylene which is unsubstituted or substituted by $C_1$–$C_4$alkyl is, for example, 1,2-, 1,3- or 1,4-phenylene. 1,4-Phenylene is preferred.

Alkanoyl having up to 25 carbon atoms is a branched or unbranched radical, for example formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. Alkanoyl having 2 to 18, in particular 2 to 12, for example 2 to 6, carbon atoms is preferred. Acetyl is particularly preferred.

$C_3$–$C_2$Alkanoyl which is interrupted by oxygen, sulfur or

is, for example, $CH_3$—O—$CH_2$CO—, $CH_3$—S—$CH_2$CO—, $CH_3$—NH$CH_2$CO—, $CH_3$—N($CH_3$)—$CH_2$CO—, $CH_3$—O—$CH_2CH_2$—O—$CH_2$CO—, $CH_3$—(O—$CH_2CH_2$—)$_2$O—$CH_2$CO—, $CH_3$—(O—$CH_2CH_2$—)$_3$O—$CH_2$CO— or $CH_3$—(O—$CH_2CH_2$—)$_4$O—$CH_2$CO—.

Alkenoyl having 3 to 25 carbon atoms is a branched or unbranched radical, for example propenoyl, 2-butenoyl, 3-butenoyl, isobutenoyl, n-2,4-pentadienoyl, 3-methyl-2-butenoyl, n-2-octenoyl, n-2-dodecenoyl, iso-dodecenoyl, oleoyl, n-2-octadecenoyl or n-4-octadecenoyl. Alkenoyl having 3 to 18, in particular 3 to 12, for example 3 to 6, especially 3 to 4, carbon atoms is preferred.

Benzoyl which is substituted by $C_1$–$C_2$alkyl and preferably carries 1 to 3, in particular 1 or 2, alkyl groups is, for example, o-, m- or p-methylbenzoyl, 2,3-dimethylbenzoyl, 2,4-di-methylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-tri-methylbenzoyl, 2,6-dimethyl-4-tert-butylbenzoyl or 3,5-di-tert-butylbenzoyl. Preferred substituents are $C_1$–$C_8$alkyl, in particular $C_1$–$C_4$alkyl.

Compositions which are of interest are those comprising compounds of the formula I in which $R_1$, $R_2$, $R_3$, $R_4$, $R_8$, $R_6$, $R_7$ and $R_8$ independently of one another are hydrogen, chlorine, $C_1$–$C_{18}$alkyl or $C_2$–$C_{18}$alkyl which is interrupted by oxygen, sulfur or

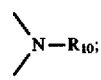

$C_5$–$C_8$-cycloalkyl which is unsubstituted or substituted by $C_1$–$C_4$alkyl; phenyl which is unsubstituted or substituted by $C_1$–$C_4$alkyl; $C_7$–$C_9$phenylalkyl, hydroxyl, $C_1$–$C_{18}$alkoxy or $C_3$–$C_{18}$-alkoxy which is interrupted by oxygen, sulfur or

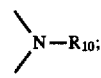

mercapto, $C_1$–$C_{18}$alkylthio, $C_1$–$C_{18}$alkanoyloxy or $C_3$–$C_8$alkanoyloxy which is interrupted by oxygen, sulfur or

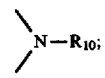

$C_3$–$C_8$alkenoyloxy, benzoyloxy or benzoyloxy which is substituted by $C_1$–$C_8$-alkyl; nitro, cyano, —($CH_2$)$_m$$COR_{11}$ or

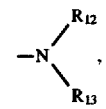

and furthermore the radicals $R_1$ and $R_2$, $R_2$ and $R_3$, $R_3$ and $R_4$, $R_5$ and $R_6$, $R_6$ and $R_7$ or $R_7$ and $R_8$, together with the carbon atoms to which they are bonded, form a benzo ring, or the same pairs of radicals together are —O($CH_2$)$_n$O—, with the condition that at least one of the radicals $R_1$, $R_2$, $R_3$ or $R_4$ and at least one of the radicals $R_5$, $R_6$, $R_7$ or $R_8$ is hydrogen, $R_1$ is additionally a radical of the formula II, $R_2$ is additionally a radical of the formula III, $R_3$ is additionally a radical of the formula IV and $R_4$ is additionally a radical of the formula V, and in which at the same time only one radical of the formula II, III, IV or V occurs in the compound of the formula I

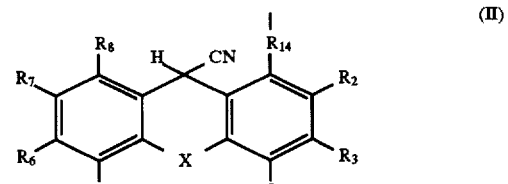

(II)

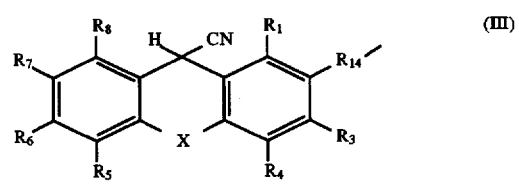

(III)

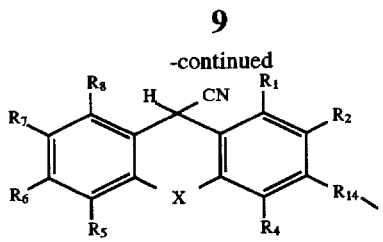 (IV)

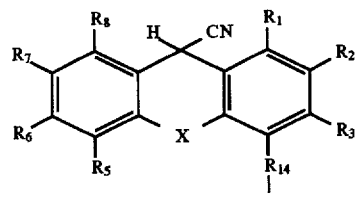 (V)

$R_{11}$ is hydroxyl, $C_1$-$C_{12}$alkoxy or

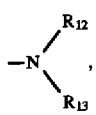

$R_{12}$ and $R_{13}$ independently of one another are hydrogen or $C_1$-$C_{12}$alkyl, $R_{14}$ is a direct bond, $C_{1-C2}$alkylene or $C_2$-$C_2$alkylene which is interrupted by oxygen, sulfur or

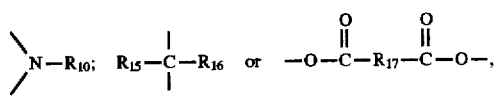

$R_{15}$ and $R_{16}$ independently of one another are hydrogen, $C_1$-$C_8$alkyl or phenyl, or $R_{15}$ and $R_{16}$, together with the C atom to which they are bonded, form a $C_5$-$C_7$cycloalkylidene ring which is unsubstituted or substituted by 1 to 3 $C_1$-$C_4$alkyl groups, $R_{17}$ is a direct bond, $C_1$-$C_{12}$alkylene or $C_2$-$C_{12}$alkylene which is interrupted by oxygen, sulfur or

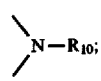

$C_2$-$C_{12}$alkenylene, $C_2$-$C_{16}$alkylidene, $C_7$-$C_{12}$phenylalkylidene, $C_5$-$C_7$phenylene which is unsubstituted or substituted by $C_1$-$C_4$alkyl or

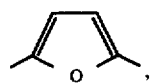

$R_{18}$ is hydrogen, $C_1$-$C_{18}$alkyl or $C_2$-$C_{18}$alkyl which is interrupted by oxygen, sulfur or

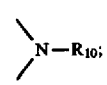

$C_5$-$C_7$cycloalkyl which is unsubstituted or substituted by $C_1$-$C_4$alkyl; phenyl which is unsubstituted or substituted by $C_1$-$C_4$alkyl; $C_7$-$C_9$phenylalkyl, hydroxyl, $C_1$-$C_{12}$alkoxy or $C_3$-$C_{12}$alkoxy which is interrupted by oxygen, sulfur or

$C_1$-$C_{18}$alkenoyl or $C_3$-$C_{18}$alkanoyl which is interrupted by oxygen, sulfur or

$C_3$-$C_{18}$alkenoyl, benzoyl or benzoyl which is substituted $C_1$-$C_8$alkyl; cyano, —$(CH_2)_mCOR_{11}$ or

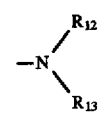

and $R_{19}$ is $C_1$-$C_{18}$alkyl, benzyl or —$CH_2CH_2OH$.

Preferred compositions are those comprising compounds of the formula I in which $R_5$, $R_6$, $R_7$ and $R_8$ are hydrogen.

Preferred compositions are also those comprising compounds of the formula I in which X is a direct bond, oxygen, sulfur, —$CH_2CH_2$—, —CH=CH—,

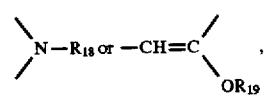

$R_{18}$ is $C_1$-$C_4$alkyl and $R_{19}$ is $C_1$-$C_8$alkyl or —$CH_2CH_2OH$.

Compositions which are likewise preferred are those comprising compounds of the formula I in which $R_1$, $R_2$, $R_3$ and $R_4$ independently of one another are hydrogen, chlorine, $C_1$-$C_{18}$alkyl or $C_2$-$C_{18}$alkyl which is interrupted by oxygen; $C_5$-$C_8$cycloalkyl, phenyl, $C_7$-$C_9$phenylalkyl, hydroxyl, $C_1$-$C_{18}$alkoxy or $C_3$-$C_{18}$alkoxy which is interrupted by oxygen; $C_1$-$C_{18}$alkylthio, $C_1$-$C_{18}$alkanoyloxy or $C_3$-$C_{18}$alkanoyloxy which is interrupted by oxygen; $C_3$-$C_{18}$alkenoyloxy, benzoyloxy, cyano, —$(CH_2)_mCOR_{11}$ or

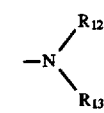

with the condition that at least one of the radicals $R_1$, $R_2$, $R_3$ or $R_4$ is hydrogen, $R_2$ is additionally a radical of the formula III and $R_4$ is additionally a radical of the formula V, and in which at the same time only one radical of the formula III or V occurs in the compound of the formula I

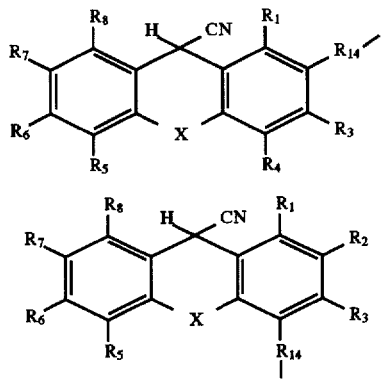

(III)

(V)

$R_5$, $R_6$, $R_7$ and $R_8$ independently of one another are hydrogen, chlorine, $C_1$–$C_{18}$alkyl, $C_5$–$C_8$cycloalkyl, phenyl, benzyl, hydroxyl, $C_1$–$C_{18}$alkylthio, $C_1$–$C_{18}$alkylthio, $C_1$–$C_{18}$alkanoyloxy, $C_3$–$C_{18}$alkenoyloxy, benzoyloxy, cyano, —$(CH_2)_m$COR$_{11}$or

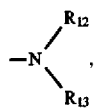

with the condition that at least one of the radicals $R_5$, $R_6$, $R_7$ or $R_8$ is hydrogen.

$R_{11}$ is $C_1$–$C_{12}$alkoxy or

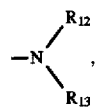

$R_{12}$ and $R_{13}$ independently of one another are hydrogen or $C_1$–$C_8$alkyl, $R_{14}$ is $C_1C_8$alkylene or $C_2$–$C_{12}$alkylene which is interrupted by oxygen;

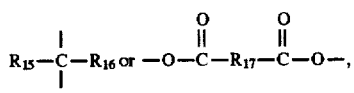

$R_{15}$ and $R_{16}$ independently of one another are hydrogen, $C_1C_8$alkyl or phenyl, or $R_{15}$ and $R_{16}$, together with the C atom to which they are bonded, form a $C_5$–$C_7$cycloalkylidene ring and $R_{17}$ is $C_1$–$C_8$alkylene or $C_2$–$C_8$alkylene which is interrupted by oxygen; $C_2$–$C_8$alkenylene, $C_2$–$C_8$alkylidene, $C_5$–$C_7$cycloalkylene or phenylene.

Compositions which are of particular interest are those comprising compounds of the formula I in which $R_1$, $R_2$, $R_3$ and $R_4$ independently of one another are hydrogen, $C_1$–$C_{18}$alkyl, $C_5$–$C_8$cycloalkyl, phenyl, $C_7$–$C_9$phenylalkyl, hydroxyl, $C_1$–$C_{18}$alkoxy, $C_1$–$C_8$alkanoyloxy, $C_3$–$C_{18}$-alkenoyloxy, benzoyloxy, cyano or —$(CH_2)_m$COR$_{11}$, with the condition that at least one of the radicals $R_1$, $R_2$, $R_3$ or $R_4$ is hydrogen, $R_2$ is additionally a radical of the formula III and $R_4$ is additionally a radical of the formula V, and in which at the same time only one radical of the formula III or V occurs in the compound of the formula I

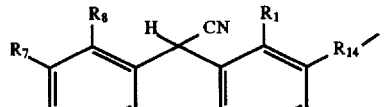

(III)

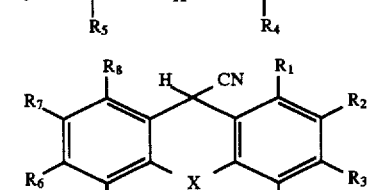

(V)

$R_5$, $R_6$, $R_7$ and $R_8$ independently of one another are hydrogen, chlorine, $C_1$–$C_{18}$alkyl, $C_5$–$C_8$cycloalkyl, phenyl, benzyl or cyano, with the condition that at least one of the radicals $R_5$, $R_6$, $R_7$ or $R_8$ is hydrogen, $R_{11}$ is $C_1$–$C_{12}$alkoxy, $R_{14}$ is $C_1$–$C_8$alkylene, $C_2$–$C_{12}$alkylene which is interrupted by oxygen or

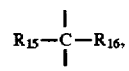

$R_{15}$ and $R_{16}$ independently of one another are hydrogen, $C_1$–$C_8$alkyl or phenyl, or $R_{15}$ and $R_{16}$, together with the C atom to which they are bonded, form a $C_5$–$C_7$cycloalkylidene ring, $R_{18}$ is hydrogen, $C_1$–$C_{12}$alkyl, benzyl, hydroxyl, $C_1$–$C_{12}$alkoxy, $C_1$–$C_{18}$alkanoyl or benzoyl, X is a direct bond, oxygen, sulfur, —$CH_2CH_2$—, —CH=CH— or

and m is 0 or 1.

Compositions which are particularly preferred are those comprising compounds of the formula I in which $R_1$, $R_2$, $R_3$ and $R_4$ independently of one another are hydrogen, $C_2$–$C_8$alkyl, cyclohexyl, $C_7$–$C_9$phenylalkyl, hydroxyl, $C_1$–$C_{12}$alkoxy, $C_5$–$C_8$alkanoyloxy or —$(CH_2)_mCOR_{11}$, with the condition that at least one of the radicals $R_1$, $R_2$, $R_3$ or $R_4$ is hydrogen, $R_5$, $R_6$, $R_7$ and $R_8$ independently of one another are hydrogen, chlorine, $C_1$–$C_{18}$alkyl or cyclohexyl, with the condition that at least one of the radicals $R_5$, $R_6$, $R_7$ or $R_8$ is hydrogen, $R_{11}$ is $C_1$–$C_{12}$alkoxy, $R_{18}$ is hydrogen, $C_1$–$C_8$alkyl, hydroxyl, $C_1$–$C_6$alkanoyl or benzoyl, X is a direct bond, oxygen, sulfur, —$CH_2CH_2$—, —CH=CH— or

and m is 0 or 1.

Compositions which are especially preferred are those comprising compounds of the formula I in which $R_1$ is hydrogen, hydroxyl, or $C_1$–$C_{12}$alkanoyloxy, $R_2$ is hydrogen, $C_1$–$C_{12}$alkyl, $C_7$–$C_9$phenylalkyl, $C_1$–$C_3$alkoxy or —$(CH_2)_m COR_{11}$, $R_3$ is hydrogen, hydroxyl or $C_1$–$C_{12}$alkanoyloxy, $R_4$ is hydrogen, $C_1$–$C_4$alkyl or cyclohexyl, with the condition that at least one of the radicals $R_1$, $R_2$, $R_3$ or $R_4$ is hydrogen, $R_5$, $R_6$, $R_7$ and $R_8$ are hydrogen, $R_{11}$ is $C_1$–$C_{12}$alkoxy, $R_{18}$ is $C_1C_4$alkyl, X is a direct bond, oxygen, sulfur, —$CH_2CH_2$—, —CH=CH— or and

and m is 0 or 1.

The compounds of the formula I are suitable for stabilizing organic materials against thermal, oxidative or light-induced degradation.

Examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholares, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPFdHDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrener/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and mines or the acyl derivatives or acetals thereof, for example polyvinyl alcohol, polyvinyl acetate, polyvinyl stearate, poly-vinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Preferred organic materials are polymers, for example natural, semi-synthetic or synthetic polymers, in particular thermoplastic polymers, tackifiers or adhesives. Polyolefins, for example polypropylene or polyethylene, are particularly preferred.

The action of the compounds according to the invention against thermal and oxidative degradation, especially during exposure to heat such as occurs in the processing of thermoplastics, is to be emphasized in particular. The compounds according to the invention are therefore outstandingly suitable as processing stabilizers.

The compounds of the formula I are preferably added to the material to be stabilized in amounts of 0.0005 to 5%, in particular 0.001 to 2%, for example 0.01 to 2%, based on the weight of organic material to be stabilized.

In addition to the compounds of the formula I, the compositions according to the invention can contain other costabilizers, for example the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4- dimethyl-6-(1'-methylundec-1'-yl)phenol, 2,4-dimethyl-6-(1'-methylheptadec-1-yl)phenol, 2,4-methyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxyphenol, 2,5-di-ten-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxy-anisole, 3,5-di-ten-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodihens, for example 2,2'-thiobis(6-tert-butyl-4-methyl-phenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,β-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis-(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.6. O-, N- and S-benzyl compounds, for example 3,5,3',5'-tetra-tert-butyl-4,4'-dihydroxy-dibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxy-anilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5tris(3,5-di-tert-butyl-4-hydroxyphenylpropinoyl)hexahydro-1,3,5triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzyl-phosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenl) proionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5-dicyclohexy-1-4-hydroxyphenyl) propionic acid with mono- or poly-hydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-buty-1-4-hydroxyphenyl) propionic acid e.g. N,N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3-tert-butyl-2'-hydroxy-5'-(2-methoxycarbonylethyl) phenyl)-5-chloro-benzotriazole, 2-(3'-tert-butyl-2'-hydroxy-5'-2-methoxycarbonylethyl)phenyl)benzotriazole, 2-(3'-tert-butyl-2'-hydroxy-5'-(2-octyl-oxycarbonylethyl)phenyl) benzotriazole, 2-(3'-tert-butyl-5'-[2-(2-ethylhexyloxy) carbonyl-ethyl]-2'-hydroxyphenyl)benzotriazole, 2-(3'-dodecyl-2'-hydroxy-5'-methylphenyl)benzo; triazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxy-phenyl]-2H-benzotriazole with polyethylene glycol 300; [R—CH$_2$CH$_2$—COO(CH$_2$)$_3$]—, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-α-methoxycinnamate, butyl α-cyano-β-methyl-p-methoxy-cinnamate, methyl α-carbomethoxy-p-methoxycinnamate and N-(β-carbomethoxy-13-cyanovinyl) -2-methylindoline.

2.5. Nickel compounds, for example nickel complexes of 2,2'-thio-bis-[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl) sebacate, bis(1,2,2,6,6-pentarnethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-penta-methylpiperidyl)-2-n-butyl-2-(2-hydroxy-3,5-di-tert-butylbenzyl)-malonate, 3-n-octyl-7,7,9,9-tetramethyl-1,3,8-triazasprio[4.5]decan-2, 4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1, 3,5-triazine, the condensate of 2-chloro-4,6-bis (4-n-butylamino-2,2,6,6-tetramethylpiperidyl)-1,3,5-triazine and 1,2-bis(3-aminopropylamino)-ethane, the condensate of 2-chloro-4,6-di-(4-n-butylamino-1,2,2,6,6-pentamethylpiperi-dyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2, 5-dione, 3-dodecyl-1-(1,2,2,6,6-pentamethyl-4-piperidyl) pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis (3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2-hydroxy-3-butyloxy-propoxy)phenyl]-4,6-bis(2,4-dimethyl) -1,3,5-triazine, 2-[2-hydroxy-3-octyloxy-propyloxy)phenyl] -4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenyl-propionyl) hydrazine, 3-salicyloylamino-1, 2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaeryt hritol diphosphite, diisodecyloxypentaerythritol diphosphite, bis(2,4-di-tert-butyl-6-methylphenyl)pentaerythritol diphosphite, bis(2,4, 6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetratert-butyl-12H-dibenz[d,g]-1,3,2-dioxaphosphocin, 6-fluoro-2,4,8,10tetra-tert-butyl-12-methyl-dibenz[d,g]-1,3, 2-dioxaphosphocin, bis(2,4-di-tert-butyl-6-methylphenyl) methylphosphite, bis(2,4-di-tert-butyl-6-methylphenyl) ethylphosphite.

5. Peroxide scaven eg, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmirate, antimony pyrocatecholate or tin pyrocatecholate. 8. Nucleating agents, for example, 4-tert-butylbenzoic acid, adipic acid, diphenylacetic acid.

9. Fillers and reinforcin aents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. No. 4,325,863, U.S. Pat. No. 4,338, 244 or U.S. Pat. No. 5,175,312, or 3-[4-(2-acetoxyethoxy) phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy-]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The costabilizers are added, for example, in concentrations of 0.01 to 10%, based on the total weight of the material to be stabilized.

Other preferred compositions additionally also comprise, in addition to component (a) and the compounds of the formula I, further additives, in particular phenolic antioxidants, light stabilizers and/or processing stabilizers.

Particularly preferred additives are phenolic antioxidants (point 1 of the list), sterically hindered amines (point 2.6 of the list), phosphites and phosphonites (point 4 of the list) and peroxide-destroying compounds (point 5 of the list).

The compounds of the formula I and if appropriate further additives are incorporated into the polymeric organic material by known methods, for example before or during shaping, or by application of the dissolved or dispersed compounds to the polymeric organic material, if appropriate with subsequent evaporation of the solvent. The compounds of the formula I can also be added in the form of a masterbatch, which comprises them, for example, in a concentration of 2.5 to 25% by weight, to the materials to be stabilized.

The compounds of the formula I can also be added before or during the polymerization or before the crosslinking.

The compounds of the formula I can be incorporated into the material to be stabilized in the pure form or in a form encapsulated in waxes, oils or polymers.

The compounds of the formula I can also be sprayed onto the polymer to be stabilized. They are capable of diluting other additives (for example the abovementioned conventional additives) or melts thereof such that they can also be sprayed together with these additives onto the polymer to be stabilized. Addition by spraying on during deactivation of the polymerization catalysts is particularly advantageous, it being possible to use, for example, the steam used for deactivation for the spraying.

In the case of spherically polymerized polyolefins, it may be advantageous, for example, to apply the compounds of the formula I by spraying, if appropriate together with other additives.

The materials stabilized in this way can be used in widely varying forms, for example as films, fibres, tapes, moulding compositions or profiles or as binders for paints, adhesives or putties.

The present invention also relates to a process for stabilizing an organic material against oxidative, thermal or light-induced degradation, which is characterized in that at least one compound of the formula I is incorporated into or applied to this material.

As already emphasized, the compounds according to the invention are particularly advantageously employed as stabilizers in polyolefins in particular as heat stabilizers. Excellent stabilization is obtained, for example, if they are employed in combination with organic phosphites or phosphonites. The compounds according to the invention have the advantage here that they are already effective in exceptionally small amounts. They are employed, for example, in amounts of 0.0001 to 0.015, in particular 0.0001 to 0.008% by weight, based on the polyolefin. The organic phosphite or phosphonite is advantageously employed in an amount of 0.01 to 2, in particular 0.01 to 1% by weight, likewise based on the polyolefin. The organic phosphites or phosphonites employed are preferably those such as are described in German Offenlegungsschrift DE-A-42 02 276. In that specification see in particular the patent claims, the examples and page 4, last paragraph, to page 8. Particularly advantageous phosphites and phosphonites are also to be found in point 4 of the above list of costabilizers.

An especially excellent stabilization of polyolefins is obtained, for example, if the compounds according to the invention are employed in a three-component combination with organic phosphites or phosphonites and with a phenolic antioxidant.

The invention likewise relates to novel compounds of the formula Ia

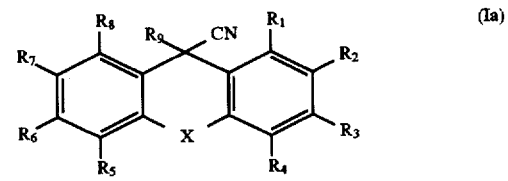

in which $R_1$, $R_2$, $R_3$, $R_4$, $R_8$, $R_6$, $R_7$ and $R_8$ independently of one another are hydrogen, $C_1$–$C_{25}$alkyl or $C_2$–$C_{25}$alkyl which is interrupted by oxygen, sulfur or

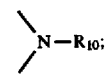

$C_5$–$C_8$cycloalkyl which is unsubstituted or substituted by $C_1$–$C_4$alkyl; phenyl which is unsubstituted or substituted by $C_1$–$C_4$alkyl, $C_7$–$C_9$phenylalkyl, hydroxyl, $C_1$–$C_{18}$alkoxy or $C_3$–$C_{18}$alkoxy which is interrupted by oxygen, sulfur or

mercapto, $C_1$–$C_{18}$alkylthio or $C_3$–$C_{18}$alkylthio which is interrupted by oxygen, sulfur or

$C_1$–$C_{25}$alkanoyloxy or $C_3$–$C_{25}$alkanoyloxy which is interrupted by oxygen, sulfur or

$C_3$–$C_{25}$alkenoyloxy, benzoyloxy or benzoyloxy which is substituted by $C_1$–$C_{12}$alkyl; nitro, cyano or —(CH$_2$)$_m$COR$_{11}$, and furthermore the radicals $R_1$ and $R_2$, $R_2$ and $R_3$, $R_3$ and $R_4$, $R_5$ and $R_6$, $R_6$ and $R_7$ or $R_7$ and $R_8$, together with the carbon atoms to which they are bonded, form a benzo ring, or the same pairs of radicals together are —O(CH$_2$)$_n$O—, with the contrition that at least one of the radicals $R_1$, $R_2$, $R_3$ or $R_4$ and at least one of the radicals $R_5$, $R_6$, $R_7$ or $R_8$ is hydrogen, at least one of the radicals $R_1$, $R_2$, $R_3$, $R_4$, $R_5$, $R_6$, $R_7$ and $R_8$ is other than hydrogen, and if $R_1$, $R_2$ or $R_3$ is methyl or methoxy, at least one of the radicals $R_4$, $R_8$, $R_6$, $R_7$ or $R_8$ is other than hydrogen, $R_I$ is additionally a radical of the formula IIa, $R_2$ is additionally a radical of the formula IIIa, $R_3$ is additionally a radical of the formula IVa and $R_4$ is additionally a radical of the formula Va, and in which at the same time only one radical of the formula IIa, IIIa, IVa or Va occurs in the compound of the formula Ia

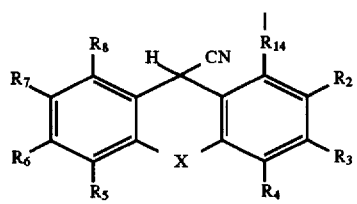

(IIa)

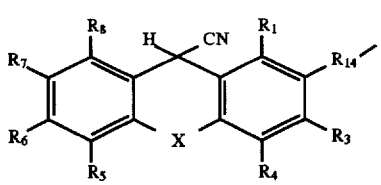

(IIIa)

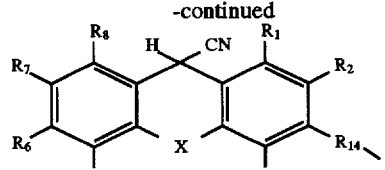

(IVa)

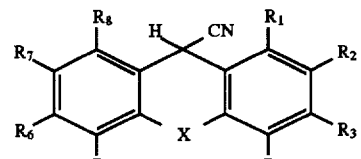

(Va)

$R_9$ is hydrogen or a radical of the formula VIa

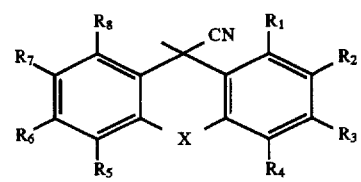

(VIa)

in which $R_1$, $R_2$, $R_3$ and $R_4$ are not a radical of the formula IIa, IIIa, IVa or Va, $R_{10}$ is hydrogen or $C_1$–$C_8$alkyl, $R_{11}$ is hydroxyl, $C_1$–$C_{18}$alkoxy or

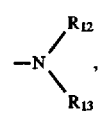

$R_{12}$ and $R_{13}$ independently of one another are hydrogen or $C_1$–$C_{18}$alkyl, $R_{14}$ is a direct bond, $C_1$–$C_{18}$alkylene or $C_2$–$C_{18}$alkylene which is interrupted by oxygen, sulfur or

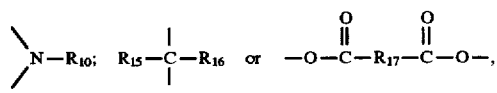

$R_{15}$ and $R_{16}$ independently of one another are hydrogen, CF$_3$, $C_1$–$C_{12}$alkyl or phenyl, or $R_{15}$ and $R_{16}$, together with the C atom to which they are bonded, form a $C_5$–$C_8$cycloalkylidene ring which is unsubstituted or substituted by 1 to 3 $C_1C_4$alkyl groups, $R_{17}$ is a direct bond, $C_1$–$C_{18}$alkylene or $C_2$–$C_{18}$alkylene which is interrupted by oxygen, sulfur or

$C_2$–$C_{18}$alkenylene, $C_2$–$C_{18}$alkylidene, $C_7$–$C_{20}$phenylalkylidene, $C_2$–$C_{25}$cycloalkylene, $C_7$–$C_8$bicycloalkylene, phenylene which is unsubstituted or substituted by $C_1$–$C_4$alkyl

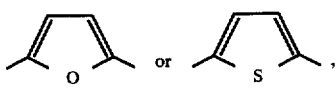

$R_{18}$ is hydrogen, $C_1$–$C_{25}$alkyl or $C_2$–$C_{25}$alkyl which is interrupted by oxygen, sulfur or

$C_2$–$C_{25}$cycloalkyl which is unsubstituted or substituted by $C_1C_4$alkyl; phenyl which is unsubstituted or substituted by $C_1C_4$alkyl; $C_7C_9$phenylalkyl, hydroxyl, $C_1$–$C_{18}$-alkoxy or $C_3$–$C_{18}$alkoxy which is interrupted by oxygen, sulfur or

$C_1C_{25}$alkanoyl or $C_3C_{25}$alkylnoyl or $C_3$–$C_{25}$salkanoyl which is interrupted by oxygen, sulfur or

$C_1C_{25}$alkanoyl, benzoyl or benzoyl which is substituted by $C_1C_{12}$alkyl; cyano, —$(CH_2)_m$COR or

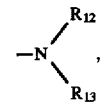

$R_{19}$ is $C_1C_{25}$alkyl, $C_7C_9$phenylaylkyl or —$CH_2CH_2OH$, X is a direct bond, oxygen, sulfur, —SO—, —$SO_2$—, —$CH_2$—, —$CH_2CH_2$—, —CH=CH—,

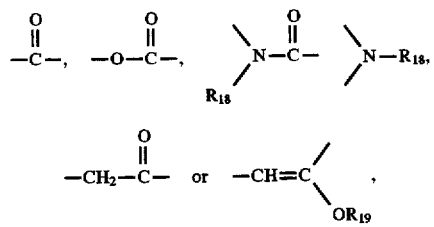

m is 0, 1 or 2 and
n is 1 or 2.

Preferred groups of novel compounds of the formula Ia correspond to those in the preferred definitions expressed above for the compositions according to the invention.

Compounds of the formula Ia which are furthermore preferred are those in which $R_5$, $R_6$, $R_7$ and $R_8$ are hydrogen, with the condition that at least one of the radicals $R_1$, $R_2$, $R_3$ or $R_4$ is other than hydrogen and none of the radicals $R_1$, $R_2$ and $R_3$ is methyl or methoxy.

Particularly preferred compounds of the formula Ia are those in which $R_1$, $R_2$, $R_3$ and $R_4$ independently of one another are hydrogen, $C_4$–$C_{18}$alkyl, $C_5C_8$cycloalkyl, phenyl, $C_7C_9$phenylalkyl, hydroxyl, $C_3C_{18}$alkoxy, $C_1$–$C_8$alkanoyloxy, $C_3C_{18}$alkenoyloxy, benzoyloxy, cyano or —$(CH_2)_m$COR$_{11}$, with the condition that at least one of the radicals $R_1$, $R_2$, $R_3$ or $R_4$ is hydrogen. $R_2$ is additionally a radical of the formula and $R_4$ is additionally a radical of the formula Va, and in which at the same time only one radical of the formula IIIa or Va occurs in the compound of the formula Ia

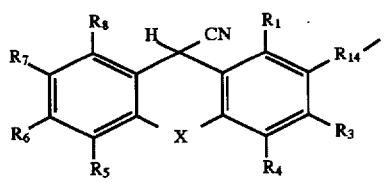

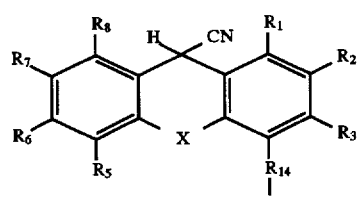

$R_5$, $R_6$, $R_7$ and $R_8$ independently of one another are hydrogen, $C_1C_{18}$alkyl, $C_5C_8$cycloalkyl, phenyl, benzyl or cyano, with the condition that at least one of the radicals $R_8$, $R_6$, $R_7$ or $R_8$ is hydrogen and at least one of the radicals $R_1$, $R_2$, $R_3$, $R_4$, $R_5$, $R_6$, $R_7$ and $R_8$ is other than hydrogen.

$R_{11}$ is $C_1C_{12}$alkoxy.

$R_{14}$ is $C_1C_8$alkylene, $C_2$–$C_{12}$alkylene which is interrupted by oxygen or

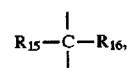

$R_{15}$ and $R_{16}$ independently of one another are hydrogen, $C_1C_8$alkyl or phenyl, or $R_{15}$ and $R_{16}$, together with the C atom to which they are bonded, form a $C_5$–$C_7$cycloalkylidene ring, $R_{18}$ is hydrogen, $C_1C_{12}$alkyl, benzyl, hydroxyl, $C_1C_{12}$alkoxy, $C_1C_{18}$alkanoyl or benzoyl, X is a direct bond, oxygen, sulfur, —$CH_2CH_2$—, —CH=CH— or

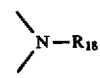

and m is 0 or 1.

The compounds of the formula I and Ia can be prepared in a manner which is known per se.

For example, a carboxylic acid of the formula VII

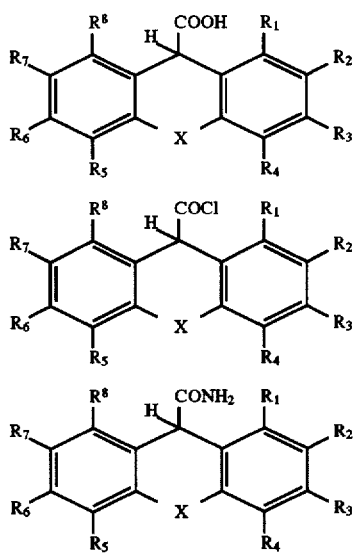

in which $R_1$, $R_2$, $R_3$, $R_4$, $R_8$, $R_6$, $R_7$ and $R_8$ are as defined and X is preferably a direct bond, is converted into the nitrile of the formula I via the acid chloride of the formula VIII and the amide of the formula IX by processes analogous to U.S. Pat. No. 3,452,076 and analogous to the specifications of M.N. Romanelli et al, II Farraaco 46(10), 1121 (1991).

If X is, for example, oxygen or sulfur, the xanthydrols or thioxanthydrols of the formula XI are reacted with, for example, potassium cyanide in acetic acid to give the compounds of the formula I by a process analogous to U.S. Pat. No. 2,956,063.

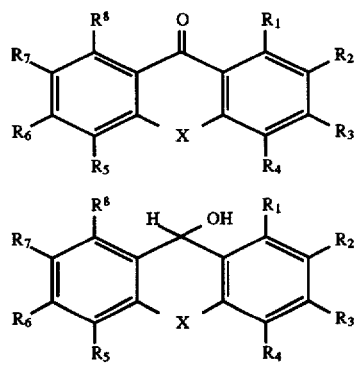

The compounds of the formula XI in which X is oxygen, sulfur, —CH$_2$CH$_2$—, —CH=CH— or

can also be reacted, for example, with trimethylsilylcyanide and a catalytic amount of zinc iodide in methylene chloride to give the compounds of the formula I or Ia by a process analogous to the specifications of K. Kobayashi et al., J. Chem. Soc. Chem. Commun. 1992, 780.

The xanthydrols and thioxanthydrols of the formula XI are known in the literature and are preferably prepared from the known xanthones and thioxanthones of the formula X (X=roman number ten) in which X (X=letter) is oxygen or sulfur, by reduction of the carbonyl group.

Xanthones and thioxanthones of the formula X are preferably prepared, for example, by ring closure of o-phenoxybenzoic acid derivatives or o-phenylthiobenzoic acid derivatives, water being split off.

Another possibility for the preparation of the compounds of the formula I and Ia relates to the reaction of known xanthylium (X=oxygen), thioxanthylium (X=sulfur) or acridinium

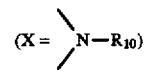

salts of the formula XII,

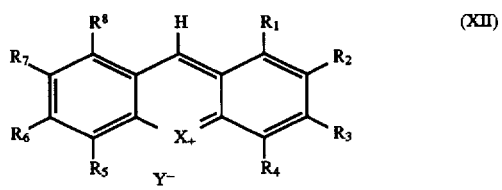

in which Y is an anion, for example halide, perchlorate or hydrogen sulfate, with cyanide, for example potassium cyanide, in an aqueous or organic solvent by a process analogous to a specification of M. Hori et at, J. Org. Chem. 45 (12), 2468 (1980).

The reaction temperatures are between room temperature and 150° C., preferably between 20° and 80° C.

The compounds of the formula I and Ia in which X is —CH$_2$CH$_2$— or —CH=CH— are prepared by a process analogous to that of V. Valenta et al, Coil. Czech. Chem. Comm. 53 (4), 860 (1988) or M. A. Davis et at, J. Med. Chem. 7, 88 (1964) starting from known halides of the formula XIII

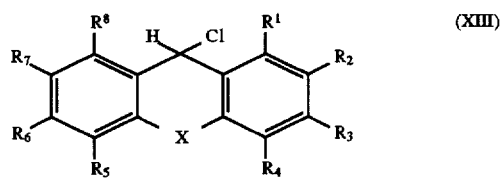

by reaction with cyanides, for example trimethylsilylcyanide or silver cyanide, and a catalytic amount of a Lewis acid, for example tin tetrachloride, in an organic solvent, for example methylene chloride or toluene.

The compounds of the formula XIII in which X is —CH$_2$CH$_2$— or —CH=CH— are known in the literature or can be prepared, for example, in an analogous manner in accordance with the method of V. Mychajlyszyn et al, Coll. Czech. Chem. Comm. 24, 3955 (1959); or G. Berti, Gazz. Chim. Ital. 87,293 (1957).

The compounds of the formula I and Ia in which X is

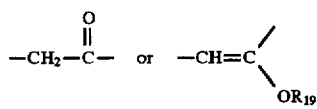

are prepared by a process analogous to that of M. A. Davis et al, Can. J. Chem. 47 (15), (1969) or U.S. Pat. No. 3,641,038.

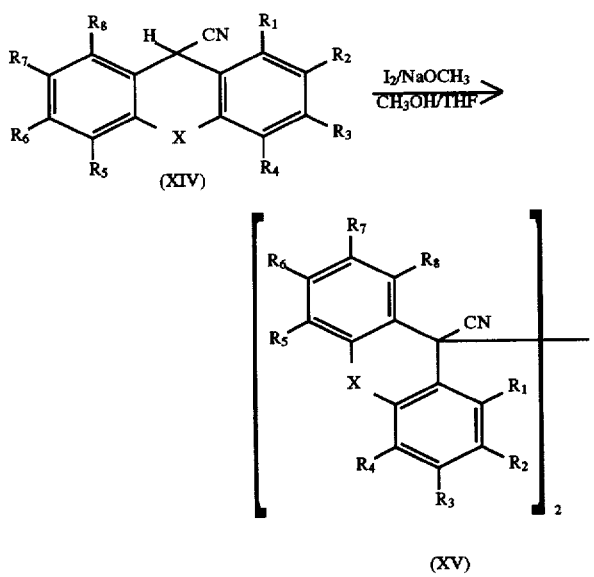

The dimerization of the compounds of the formula XIV for the preparation of compounds of the formula I and Ia in which $R_9$ is a radical of the formula VI or VIa [compounds of the formula XV] is carried out by oxidation with, for example, iodine under basic conditions in an organic solvent at room temperature. Sodium methylate is a particularly suitable base and methanol, diethyl ether or tetrahydrofuran is a suitable solvent.

The following examples illustrate the invention in more detail. Parts or percentages are by weight.

EXAMPLE 1

Preparation of 9-cyano-fluorene (compound (101), Table 1)

9-Cyano-fluorene is described in U.S. Pat. No. 3,452,076 or can be prepared by a process analogous to that of M. N. Romanelli et al, Il Farraaco 46(10), 1121 (1991).

100 ml (1.37 mol) of thionyl chloride are added to 21.0 g (0.10 mol) of fluorene-9-carboxylic acid and the mixture is refluxed for about 90 minutes. The excess thionyl chloride is evaporated off on a vacuum rotary evaporator. The residue is taken up three times with about 50 ml of toluene each time and the mixture evaporated on a vacuum rotary evaporator. The oily residue is added in portions to a mixture of about 1 kg of ice and 240 ml of concentrated ammonia solution. The fluorene-9-carboxylic acid amide which has precipitated is filtered off, washed with water and dried under a high vacuum. The dried fluorene-9-carboxylic acid areire is then added to 160 ml (1.75 mol) of phosphorus oxychloride and the mixture is refluxed for about 2 hours. The reaction mixture is cooled and concentrated on a vacuum rotary evaporator. The residue is taken up in toluene and the mixture is washed with water. The organic phases are combined, dried over sodium sulfate and concentrated on a vacuum rotary evaporator. Crystallization of the residue from cyclohexane gives 12.4 g (65%) of 9-cyano-fluorene, melting point 152°–154° C. (compound (101), Table 1).

EXAMPLE 2

Preparation of 9-cyano-xanthene (compound (102), Table 1)

The preparation of 9-cyano-xanthene is described, for example, in U.S. Pat. No. 2,956,063.

17.5 g (0.268 mol) of potassium cyanide are added in portions to a solution, heated at 50° C., of 24.2g (0.122 mol) of xanthydrol in 420 ml of acetic acid. The reaction mixture is subsequently stirred at 60° C. for 2 hours and then cooled, poured onto 400 ml of water and extracted with ethyl acetate/hexane=1:1. The organic phases are washed with water, combined, dried over sodium sulfate and concentrated on a vacuum rotary evaporator. Chromatography of the residue over silica gel using the mobile phase system hexane/ethyl acetate=19:1 and crystallization of the pure fractions from ether/petroleum ether gives 20.2 g (80%) of 9-cyano-xanthene, melting point 101° C. (compound (102), Table 1). The compounds (111), (112), (113), (114), (115), (116) and (117) are prepared analogously to Example 2 from the corresponding substituted xanthydrols and thioxanthydrols, such as, for example, 4-cyclohexyl-xanthydrol, 2-tert-butyl-xanthydrol, 2-nonyl-xanthydrol, 2-(α,α-dimethylbenzyl)-4-methyl-xanthydrol, 2-n-propoxy-xanthydrol, 2,4-diethylthioxanthydrol or 2-dodecyl-thioxanthydrol.

a) Preparation of the substituted xanthydrols and thioxanthydrols:

A solution of 13.9 g (50.0 mmol) of 4-cyclohexyl-xanthone in 150 ml of absolute tetrahydrofuran is added dropwise to a suspension of 1.4 g (36.0 mmol) of lithium aluminium hydride in 10 ml of absolute tetrahydrofuran. The reaction mixture is stirred at room temperature for 1 hour, subsequently cooled to 10° C. and diluted with 100 ml of diethyl ether, and 1.5 ml of water, 1.5 ml of a 15% aqueous sodium hydroxide solution and 4.5 ml of water are added in succession. The precipitate is filtered and the flitrate is concentrated on a vacuum rotary evaporator. 14.0 g (100%) of 4-cyclohexyl-xanthydrol result as a brown oil which can be converted into 4-cyclohexyl-9-cyano-xanthene (compound (111), Table 1) without further purification.

From the corresponding substituted xanthones and thioxanthones, for example 2-tert-butyl-xanthone, 2-nonyl-xanthone, 2-(α,α-dimethylbenzyl)-4-methyl-xanthone, 2-n-pro-poxy-xanthone, 2,4-diethyl-thioxanthone (Kayacure®DETX) or 2-dodecyl-thioxanthone (Ultracure ®DTX), respectively, 2-tert-butyl-xanthydrol, 2-nonyl-xanthydrol, 2-(α,α-di-methylbenzyl)-4-methyl-xanthydrol, 2-n-propoxy-xanthydrol, 2,4-diethyl-thioxanthydrol or 2-dodecyl-thioxanthydrol are prepared analogously to Example 2a.

b) Preparation of the substituted xanthones:

A mixture of 18.4 g (65 mmol) of 2-(2-cyclohexylphenoxy)benzoic acid and 190 g of polyphosphoric acid is kept at 100° C. for 2 hours. The reaction mixture is then diluted with 200 ml of methanol, neutralized with sodium carbonate and poured onto about 800 ml of water. The product which has precipitated is filtered off, washed with water and dried under a high vacuum. 14.6 g (77%) of 4-cyclohexylxanthone, melting point 122°–124° C., result as a beige powder.

From the corresponding substituted benzoic acids, for example 2-(4-tert-butylphenoxy)-benzoic acid, 2-(4-nonylphenoxy)benzoic acid, 2-[4-(cz,cz-dimethylbenzyl)-2'-methyl-phenoxy]benzoic acid or 2-(4-n-propoxyphenoxy)benzoic acid, 2-tert-butyl-xanthone, melting point 101°–103° C.; 2-nonyl-xanthone, oil (isomer mixture ); 2-(α,α-dimethyl-benzyl)-4-methyl-xanthone, melting point 132°–134° (22; or 2-n-propoxy-xanthone, melting point 94°–100° C.; are prepared analogously to Example 2b.

c) Preparation of the substituted benzoic acids:

A mixture of 21.4 g (0.12 mol) of sodium 2-chlorobenzoate, 26.1 g (0.132 mol) of sodium 2-cyclohexylphenolate, 4.95 g (0.05 mol) of copper(I) chloride and 16.17 g (0.05 mol) of tris[2-(2-methoxyethoxy)-ethyl]amine (TDA) in 1.5 l of diethylene glycol dimethyl ether ("diglyme") is kept at 140° C. for 8 hours. The solvent is then concentrated on a vacuum rotary evaporator and the residue is diluted with water and acidified with concentrated hydrochloric acid. The product is extracted with ethyl acetate. The organic phases are washed with water, combined, dried over sodium sulfate and concentrated on a vacuum rotary evaporator. 22.2 g (68%) of 2-(2-cyclohexylphenoxy)benzoic acid, melting point 109°–123° C., result as a beige powder.

From the corresponding substituted sodium phenolates, for example sodium 4-tert-butyl-phenolate, sodium 4-nonylphenolate, sodium 4-($\alpha,\alpha$-dimethylbenzyl)-2-methyl-phenolate or sodium 4-n-propoxyphenolate, 2-(4-tert-butylphenoxy)benzoic acid, melting point 137°–139° C.; 2-(4-nonylphenoxy)benzoic acid, oil (isomer mixture); 2-[4-($\alpha,\alpha$-dimethyl-benzyl)-2-methyl-phenoxy]benzoic acid, melting point 154°–158° C.; or 2-(4-n-propoxyphenoxy)benzoic acid, melting point 139°–144° C.; are prepared analogously to Example 2c.

EXAMPLE 3

Preparation of 9-cyano-thioxanthene (compound (103), Table 1)

The preparation of 9-cyano-thioxanthene has been described, for example, by M. Hori et al, J. Org. Chem. 45 (12), 2468 (1980).

8.0 g (27.0 mmol) of thioxanthylium perchlorate [C. C. Price et al, J. Amer. Chem. Soc. 85, 2278 (1963)] are added to a well-stiffed mixture of 3.5 g (53.8 mmol) of potassium cyanide in 4 ml of water and 30 ml of methylene chloride under a nitrogen atmosphere. After one hour, the mixture is dried over potassium carbonate and filtered and the flitrate is concentrated on a vacuum rotary evaporator. Crystallization of the residue from isopropanol gives 5.5 g (91%) of 9-cyano-thioxanthene, melting point 103°–105° C., colourless needles (compound (103), Table I).

EXAMPLE 4

Preparation of 5-cyano-10, 11-dihydro-5H-dibenzo [a,d]cycloheptene (compound (104), Table 1)

The preparation of 5-cyano-10,11-dihydro-5H-dibenzo[a,d]cycloheptene has been described, for example, by V. Valenta et al, Coll. Czech. Chem. Comm. 53 (4), 860 (1988).

6.0 g (23.0 mmol) of tin tetrachloride are slowly added to a solution of 21.1 g (92.3 mmol) of 5-chloro-10, 11-dihydro-5H-dibenzo[a,d]cycloheptene [V. Mychajlyszyn et al, Coll. Czech. Chem. Comm. 24, 3955 (1959)] and 11.3 g (114 retool)of trimethylsilylcyanide in 150 ml of methylene chloride. The reaction mixture is stirred at room temperature for 10 hours and then diluted with 150 ml of methylene chloride, and 200 ml of water are added. The organic phase is separated off, washed with dilute sodium bicarbonate solution, dried over sodium sulfate and concentrated on a vacuum rotary evaporator. Crystallization of the residue from toluene gives 18.0 g (88.9%) of 5-cyano-10,11-dihydro-5H-dibenzo[a,d]-cycloheptene, melting point 89°–90° C. (compound (104), Table 1).

EXAMPLE 5

Preparation of 5-cyano-5H-dibenzo[a,d] cycloheptene (compound (105), Table 1)

The preparation of 5-cyano-5H-dibenzo[a,d]cycloheptene has been described, for example, by M. A. Davis et at, J. Med. Chem. 7, 88 (1964).

A solution of 27.4 g (0.12 mol) of 5-chloro-5H-dibenzo [a,d]cycloheptene [G. Berti, Gazz. Chim. Ital. 87,293 (1957) ]in 250 ml of absolute toluene is added dropwise to a suspension, stirred at 35° C., of 32.4 g (0.24 mol) of silver cyanide in 250 ml of absolute toluene in the course of 3 hours. The reaction mixture is then refluxed for a further 7 hours. It is cooled to room temperature and filtered and the flitrate is concentrated on a vacuum rotary evaporator. Crystallization of the residue from hexane gives 20.0 g (76.7%) of 5-cyano-5H-dibenzo[a,d]cycloheptene, melting point 102°–104° C. (compound (105), Table 1).

EXAMPLE 6

Preparation of 9-cyano-9,10-dihydro-10-methyl-acridine (compound (106), Table 1)

The preparation of 9-cyano-9,10-dihydro-10-methyl-acridine has been described, for example, by A. Kaufmann et al, Ber. Dr. Chem. Ges. 42, 1999 (1909).

A solution of 10.0 g (43.5 mmol) of acridine chloromethylate [A. Kaufmann et al, Ber. Dt. Chem. Ges. 42, 1999 (1909)]in 100 ml of water is covered with a layer of 200 ml of diethyl ether, and a solution of 3.13 g (48.0 mmol) of potassium cyanide in 20 ml of water is added. After about 30 minutes, the ether phase is separated off, the mixture is concentrated to 50 ml on a vacuum rotary evaporator and the product which has precipitated is filtered off. Crystallization of the crude product from ethanol gives 7.10 g (75%) of 9-cyano-9,10-dihydro-10-methyl-acridine, melting point 141°–143° C. (compound (106), Table 1).

EXAMPLE 7

Preparation of 9-cyano-1,3-dihydroxy-xanthene (compound (107), Table 1)

A mixture of 15.5 g (50.0 mmol) of 1,3-dihydroxy-xanthenium bisulfam [R. K. M. Pillai et al, J. Org. Chem. 51, 717 (1986)] and 4.90 g (75.0 mmol) of potassium cyanide in 150 ml of dimethylformamide is kept at 130° C. for 2 hours. The solvent is then concentrated on a vacuum rotary evaporator and the residue is taken up in ethyl acetate. The ethyl acetate phase is washed with water, dried over sodium sulfate and concentrated on a vacuum rotary evaporator. Chromatography of the residue over silica gel using the mobile phase system hexane/ethyl acetate=3:1 and crystallization of the pure fractions from ethyl acetate gives 10.0 g (83%) of 9-cyano-1,3-dihydroxy-xanthene, melting point 211°–215° C. (compound (107), Table 1).

EXAMPLE 8

Preparation of 9-cyano-1,3-diacetoxy-xanthene (compound (108), Table 1)

A mixture of 5.50 g (23.0 mmol) of 9-cyano-1,3-dihydroxy-xanthene (Example 7, compound (107), Table 1) and 18.06 g (230 mmol) of acetyl chloride in 55 ml of toluene is kept at 80° C. for 10 hours. The reaction mixture is then concentrated gently on a vacuum rotary evaporator, 10 ml of hexane are added to the residue and the product which has precipitated is filtered off. 6.30 g (85%) of 9-cyano-1,3-diacetoxy-xanthene, melting point 160°–161° C. (compound (108), Table 1) result.

From the corresponding acid chlorides, for example pivaloyl chloride or lauroyl chloride, the compounds (109) or (110) are prepared analogously to Example 8.

EXAMPLE 9

Preparation of 9,9'-dicyano-9,9'-bis-xanthene (compound (118), Table 1)

19.4 ml (0.105 mol) of a 5.4 molar solution of sodium methylate in methanol are added dropwise to a solution of 20.7 g (0.10 mol) of 9-cyano-xanthene (Example 2, compound (102), Table 1) in 100 ml of tetrahydrofuran. The yellow solution is stirred at room temperature for about 10 minutes and then cooled to +5° C., and a solution of 13.0 g (0.051 mol) of iodine in 60 ml of tetrahydrofuran is added dropwise. The reaction mixture is then stirred at room temperature for 2 hours. It is concentrated gently on a vacuum rotary evaporator, water is added and the mixture is extracted with ethyl acetate. The organic phases are washed with water, combined, dried over sodium sulfate and concentrated on a vacuum rotary evaporator. Crystallization of the residue from toluene gives 7.5 g (36%) of 9,9'-dicyano-9,9'-bis-xanthene, melting point 225° C. (compound (118), Table 1).

EXAMPLE 10

Preparation of n-dodecyl 9-cyano-9H-xanthene-2-carboxylate (compound (119), Table 1)

A solution of 8.21 g (20 mmol) of n-dodecyl 9-hydroxy-9H-xanthene-2-carboxylate (Example 10a) in 25 ml of methylene chloride is added dropwise to a solution, cooled to 0° C., of 3.97 g (40 mmol) of trimethylsilyl cyanide and 0.19 g (0.6 mmol) of zinc iodide in 10 ml of methylene chloride. The reaction mixture is stirred at 0°–5° C. for 30 minutes and then poured onto an aqueous saturated sodium bicarbonate solution. The product is extracted with methylene chloride. The organic phases are washed with water, combined, dried over sodium sulfate and concentrated on a vacuum rotary evaporator. The resulting solid crude product is purified by being suspended in cold ethanol. After drying under a high vacuum, 6.94 g (83%) of n-dodecyl 9-cyano-9H-xanthene-2-carboxylate, melting point 65°–66.5° C. (compound (119), Table 1) are obtained as a white powder.

Compound (120), Table 1, melting point 76.5°–78° C., is prepared analogously to Example 10 from ethyl 9-hydroxy-9H-xanthene-2-acetate (Example 10b).

a) Preparation of n-dodecyl 9-hydroxy-9H-xanthene-2-carboxylate. 2.6 g (0.12 mol) of lithium borohydride are added in portions to a solution of 16.34 g (0.04 mol) of n-dodecyl 9-oxo-9H-xanthene-2-carboxylate (Example 10c) in 150 ml of absolute tetrahydrofuran at room temperature. The reaction mixture is stirred at room temperature for 4 hours and then poured carefully onto an aqueous saturated ammonium chloride solution. The product is extracted with ethyl acetate. The organic phases are washed with a saturated aqueous sodium chloride solution, combined, dried over sodium sulfate and concentrated on a vacuum rotary evaporator. The resulting solid crude product is purified by being suspended in hexane. After drying under a high vacuum, 12.91 g (79%) of n-dodecyl 9-hydroxy-9H-xanthene-2-carboxylate, melting point 60°–62° C., are obtained as a white powder.

b) Preparation of ethyl 9-hydroxy-9H-xanthene-2-acetate.

5.67 g (150 mmol) of sodium borohydride are added in portions to a solution of 14.2 g (50 mmol) of ethyl 9-oxo-9H-xanthene-2-acetate (Example 10d) in 130 ml of ethanol. The suspension is stirred at room temperature for 15 hours, subsequently diluted with 80 ml of ethanol and poured onto water. The product is extracted with ethyl acetate. The organic phases are washed with an aqueous saturated sodium chloride solution, combined, dried over sodium sulfate and concentrated on a vacuum rotary evaporator. The solid residue is suspended in ethanol, the suspension is filtered and the product is dried under a high vacuum. 6.1 g (43%) of ethyl 9-hydroxy-9H-xanthene-2-acetate, melting point 214°–219° C., results as a white powder.

c) Preparation of n-dodecyl 9-oxo-9H-xanthene-2-carboxylate.

A mixture of 29.9 g (0.11 mol) of 2-(4-carboxyphenoxy) benzoic acid (Example 10e) and 250 ml of concentrated sulfuric acid is heated at 80° C. for one hour. The resulting solution is then poured onto about 2.5 litres of water and the mixture is stirred vigorously for 30 minutes. The product which has precipitated is filtered off, washed with water and dried under a high vacuum. 23.15 g (85%) of 9-oxo-9H-xanthene-2-carboxylic acid, melting point >280° C., result as a beige powder.

A mixture of 12.01 g (50 mmol) of the above 9-oxo-9H-xanthene-2-carboxylic acid, 77.4 g (420 mmol) of n-dodecanol and 0.2 g (2 mmol) of concentrated sulfuric acid is kept at 140° C. for 6 hours. The sulfuric acid is neutralized with 0.33 g (4 mmol) of sodium acetate and the excess n-dodecanol is removed by distillation (98° C./0.1 mbar). The brown residue is taken up in isopropanol and the product which has precipitated is filtered off and dried under a high vacuum. 16.7 g (82%) of n-dodecyl 9-oxo-9H-xanthene-2-carboxylate, melting point 79°–81° C., result as a beige powder.

d) Preparation of ethyl 9-oxo-9H-xanthene-2-acetate.

9-Oxo-9H-xanthene-2-acetic acid, melting point 226°–228° C., is prepared from 2-(4-carboxymethylphenoxy)benzoic acid (Example 10f) analogously to Example 10c and is reacted with ethanol to give ethyl 9-oxo-9H-xanthene-2-acetate, melting point 97°–98° C.

e) Preparation of 2-(4-carboxyphenoxy)benzoic acid.

A mixture of 40 g (0.22 mol) of the disodium salt of 4-hydroxybenzoic acid, 54 g (0.2 mol) of sodium 2-iodobenzoate, 1.98 g (0.02 mol) of copper(I) chloride and 6.47 g (0.02 mol) of tris-[2-(2-methoxyethoxy)-ethyl]amine (TDA) in 500 ml of N-methylpyrrolidone is kept at 180° C. for 4 hours. The solvent is then removed by distillation, the residue is diluted with about 1 litre of water and hthchloric acid. The product w concentrated hydrochloric acid. The product which has precipitated is filtered off and dried under a high vacuum. 29.7 g (58%) of 2-(4-carboxyphenoxy) benzoic acid, melting point 220°–223° C., result as a brown powder.

f) Preparation of 2-(4-carboxymethylphenoxy)benzoic acid.

2-(4–Carboxymethyl-phenoxy)benzoic acid, melting point 175°–179° C., is prepared analogously to Example 10e from the disodium salt of 4-hydroxyphenylacetic acid with sodium 2-iodobenzoate.

TABLE 1

| No. | Compound | Melting point (°C.) | C (%), H (%), N (%), S (%) (calculated/found) | | | |
|---|---|---|---|---|---|---|
| 101 | 9-cyanofluorene | 152–154 | 87.93<br>87.70 | 4.74<br>4.78 | 7.32<br>7.08 | —<br>— |
| 102 | 9-cyanoxanthene | 101 | 81.14<br>81.00 | 4.38<br>4.40 | 6.76<br>6.60 | —<br>— |
| 103 | 9-cyanothioxanthene | 103–105 | 75.31<br>75.29 | 4.06<br>4.07 | 6.27<br>6.06 | 14.36<br>14.21 |
| 104 | 2,2'-ethylenebis(phenyl) cyanide derivative | 89–90 | 87.64<br>87.49 | 5.98<br>5.98 | 6.39<br>6.10 | —<br>— |
| 105 | 2,2'-ethenylenebis(phenyl) cyanide derivative | 102–104 | 88.45<br>88.35 | 5.10<br>5.11 | 6.45<br>6.37 | —<br>— |
| 106 | 10-methyl-9-cyanoacridan | 141–143 | 81.79<br>81.70 | 5.49<br>5.56 | 12.72<br>12.62 | —<br>— |
| 107 | dihydroxy xanthene cyanide | 211–215 | 70.29<br>70.22 | 3.79<br>3.80 | 5.86<br>6.10 | —<br>— |
| 108 | diacetoxy xanthene cyanide | 160–161 | 66.87<br>67.04 | 4.05<br>4.21 | 4.33<br>4.09 | —<br>— |

TABLE 1-continued

| No. | Compound | Melting point (°C.) | C (%), H (%), N (%), S (%) (calculated/found) | | | |
|---|---|---|---|---|---|---|
| 109 | [structure: xanthene with H, CN, and two O-C(=O)-C(CH₃)₃ ester groups] | 148–150 | 70.75 | 6.18 | 3.44 | — |
|  |  |  | 70.78 | 6.19 | 3.29 | — |
| 110 | [structure: xanthene with H, CN, and two O-C(=O)-(CH₂)₁₀CH₃ ester groups] | 67–68 | 75.59 | 8.85 | 2.32 | — |
|  |  |  | 75.69 | 9.18 | 2.04 | — |
| 111 | [structure: xanthene with H, CN, and cyclohexyl] | 97–98 | 83.01 | 6.62 | 4.84 | — |
|  |  |  | 82.98 | 6.54 | 4.60 | — |
| 112 | [structure: xanthene with H, CN, and C(CH₃)₃] | 67–72 | 82.10 | 6.51 | 5.32 | — |
|  |  |  | 82.12 | 6.62 | 4.80 | — |
| 113 | [structure: xanthene with H, CN, and C₉H₁₉*] | oil | 82.84 | 8.16 | 4.20 | — |
|  |  |  | 83.14 | 8.54 | 3.52 | — |
|  | *isomer mixture | | | | | |
| 114 | [structure: xanthene with H, CN, C(CH₃)₂Ph, and CH₃] | oil | 84.92 | 6.24 | 4.13 | — |
|  |  |  | 85.04 | 6.33 | 3.99 | — |
| 115 | [structure: xanthene with H, CN, and OCH₂CH₂CH₃] | 80–82 | 76.96 | 5.70 | 5.28 | — |
|  |  |  | 76.86 | 5.66 | 5.02 | — |
| 116 | [structure: thioxanthene with H, CN, and two CH₂CH₃] | oil | 77.38 | 6.13 | 5.01 | 11.47 |
|  |  |  | 77.45 | 6.12 | 4.51 | 11.49 |

TABLE 1-continued

| No. | Compound | Melting point (°C.) | C (%), H (%), N (%), S (%) (calculated/found) |
|---|---|---|---|
| 117 | 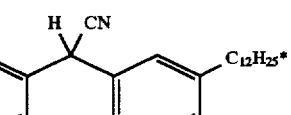 | oil | 79.74 8.49 3.58 8.19<br>79.74 8.46 3.33 8.52 |
|  | *isomer mixture |  |  |
| 118 | 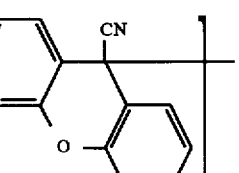 | 225 | 81.54 3.91 6.79 —<br>81.40 3.75 6.62 — |
| 119 | 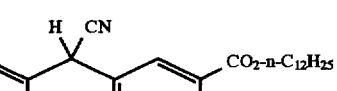 | 65–66.5 | 77.29 7.93 3.34 —<br>77.10 7.82 3.10 — |
| 120 | 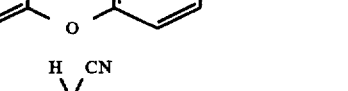 | 76.5–78 | 73.71 5.15 4.78 —<br>73.60 5.28 4.55 — |

EXAMPLE 11
Stabilization of Tackifying Resins (Tackifiers)

70 g of resin (Bevilite® 107, Bergvick) are stirred with 0.25% of the stabilizer to be tested from Table 1 at 170° C. for 10 minutes. After the formulation operation, the resin is powdered in a laboratory mixer. The resin powder is sieved to a particle size of 0.1 to 0.8 min. A portion of this resin powder is aged in open Petri dishes at 40° C. in a circulating air oven for 30 days and the hydroperoxide content is then measured. Relatively small amounts of peroxides mean better stabilization. The other portion is aged in a "twist-off glass" covered with aluminium foil at 170° C. in a circulating air oven for 48 hours and the Gardner colour is then determined. Relatively low values mean better stabilization. The results are summarized in Table 2.

TABLE 2

| Compound from Table 1 | Hydroperoxide content mmol/g | Gardner colour |
|---|---|---|
| — | 0.176 | 10–11 |
| 102 | 0.019 | 7 |
| 103 | 0.021 | 7 |
| 111 | 0.056 | 7–8 |
| 112 | 0.049 | 7–8 |
| 114 | 0.049 | 7–8 |
| 115 | 0.046 | 7 |
| 118 | 0.072 | 7 |

EXAMPLE 12
Stabilization of Styrene-based Thermoplastic Elastomers 70 g of styrene/butadiene/styrene (SBS, ®Finapren 416) are kneaded with 0.25% of the stabilizer to be tested from Table I in a Brabender plastograph at 200° C. and 60 revolutions per minute for 30 minutes. The induction time, i.e. the kneading time in minutes before the torque rises by 1 Nm after the torque minimum, is determined from the course of the torque curve. A large increase in the induction time means good stabilization. The results are summarized in Table 3.

TABLE 3

| Compound from Table 1 | Induction time in minutes |
|---|---|
| — | 5.0 |
| 102 | >100 |
| 103 | >100 |
| 111 | >100 |
| 112 | >100 |
| 113 | >100 |
| 114 | >100 |

EXAMPLE 13
Stabilization of Polybutadiene Rubber 70 g of polymer (Buna CB 529 C) is kneaded with 0.25% of the stabilizer to be tested from Table 1 in a Brabender plastograph at 160° C. and 60 revolutions per minute for 30 minutes. The induction time, i.e. the kneading time in minutes before the torque rises by 1 Nm after the torque minimum, is determined from the course of the torque curve. A large increase in the induction time means good stabilization. The results are summarized in Table 4.

TABLE 4

| Compound from Table 1 | Induction time in minutes |
|---|---|
| — | 4.4 |
| 102 | >108 |
| 111 | >108 |
| 112 | >108 |
| 113 | >108 |
| 114 | >108 |

EXAMPLE 14

Stabilization of Polypropylene During Multiple Extrusion 1.3 kg of polypropylene powder (Moplen® FL S20), which has been prestabilized with 0.015% of Irganox® 1076 (n-octadecyl 3-[3,5-di-tert-butyl-4-hydroxyphenyl] propionate) (having a melt flow index, measured at 230° C. with 2.16 kg. of 3.2) are mixed with 0.05% of Irganox® 1010 (pentaerythrityl tetrakis-[3-(3,5-di-tert-butyl-4-hydroxyphenyl)-propionate), 0.05% of calcium stearate, 0.03% of dihydrotalcite (DHT 4A®, Kyowa Chemical Industry Co., Ltd., [$Mg_{4.5}Al_2(OH)_{13}CO_3 \cdot 3.5\ H_2O$]) and 0.05% of the compound from Table 1. This mixture is extruded in an extruder having a cylinder diameter of mm and a length of 400 mm at 100 revolutions per minute, the three heating zones being set to the following temperatures: 260°, 270°, 280° C. The extradate is drawn through a waterbath for cooling and then granulated. These granules are extruded repeatedly. The melt index is measured "on line" during processing and corresponds to a value which would be measured conventionally at 230° C. with 2.16 kg/10 minutes. A large increase in the melt index means severe chain breakdown, that is to say poor stabilization. The results are summarized in Table 5.

TABLE 5

| Compound from Table 1 | Melt index after 3 extrusions |
|---|---|
| — | 17.8 |
| 101 | 4.7 |
| 102 | 4.5 |
| 111 | 4.5 |
| 112 | 4.7 |
| 113 | 4.6 |
| 114 | 4.6 |
| 115 | 4.7 |
| 116 | 4.5 |
| 117 | 4.6 |

EXAMPLE 15

Stabilization of Polyethylene During Processing 100 parts of polyethylene powder (Lupolen® 5260 Z) are mixed with 0.1 part of Irganox® 1010 (pentaerythrityl tetrakis-[3-(3,5-di-tert-butyl-4-hydroxyphenyl)-propionate] and 0.05 part of stabilizer from Table 1 and the mixture is kneaded in a Brabender plastograph at 220° C. and 50 revolutions per minute. During this time, the kneading resistance is recorded continuously as the torque. In the course of the kneading time, the polymer starts to cross-link after a relatively long period of remaining constant, which can be detected from the rapid increase in the torque. Table 6 shows the time until a noticeable increase in the torque as a measure of the stabilizer action.

TABLE 6

| Compound from Table 1 | Time until an increase in torque (minutes) |
|---|---|
| — | 5.0 |
| 111 | 38.0 |
| 112 | 37.5 |
| 114 | 43.0 |
| 115 | 41.0 |

What is claimed is:

1. A composition comprising a) an organic material subjected to oxidative, thermal or light-induced degradation and b) an effective stabilizing amount of at least one compound of the formula I

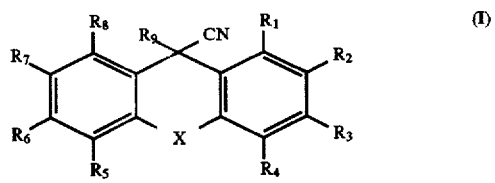

in which $R_1$, $R_2$, $R_3$, $R_4$, $R_5$, $R_6$, $R_7$ and $R_8$ independendy of one another are hydrogen, haloge or $C_2$-$C_{25}$salkyl which is interrupted by oxygen, sulfur or

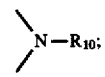

$C_5C_8$cloalkyl which is unsubstituted or substituted by $C_1C_4$alkyl; phenyl which is unsubstituted or substituted by $C_1$-$C_4$alkyl; $C_7$-$C_9$phenylalkyl, hydroxyl, $C_1C_{18}$alkoxy or $C_3C_{18}$alkoxy which is interrupted by oxygen, sulfur or

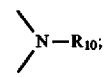

mercapto, $C_1$-$C_{18}$alkylthio or $C_3C_{18}$alkylthio which is interrupted by oxygen, sulfur or

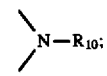

$C_1C_{25}$alkanoyloxy or $C_3C_{25}$alkanoyloxy which is interrupted by oxygen, sulfur or

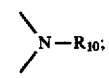

$C_3$-$C_{25}$alkenoyloxy, benzoyloxy or benzoyloxy which is substituted by $C_1C_{12}$alkyl; nitro, cyano, —$(CH_2)_m COR_{11}$ or

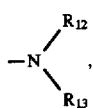

and furthermore the radicals $R_1$ and $R_2$, $R_2$ and $R_3$, $R_3$ and $R_4$, $R_5$ and $R_6$, $R_6$ and $R_7$ or $R_7$ and $R_8$, together with the carbon atoms to which they are bonded, form a benzo ring, or the same pairs of radicals together are $-O(CH_2)_nO-$, with the condition that at least one of the radicals $R_1$, $R_2$, $R_3$ or $R_4$ and at least one of the radicals $R_5$, $R_6$, $R_7$ or $R_8$ is hydrogen, R is additionally a radical of the formula II, $R_2$ is additionally a radical of the formula III, $R_3$ is additionally a radical of the formula IV and $R_4$ is additionally a radical of the formula V, and at the same time only one radical of the formula II, III, IV or V occurs in the compound of the formula I,

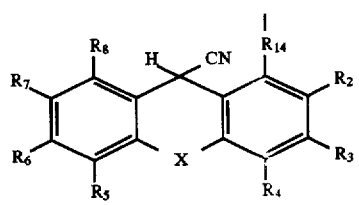 (II)

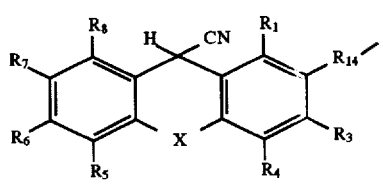 (III)

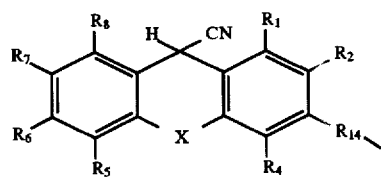 (IV)

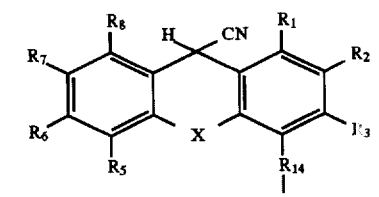 (V)

$R_9$ is hydrogen or a radical of the formula VI

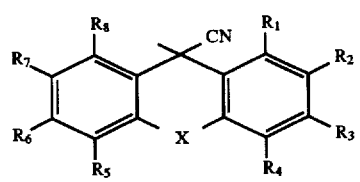 (VI)

in which $R_1$, $R_2$, $R_3$ and $R_4$ are not a radical of the formula II, III, IV or V, $R_{10}$ is hydrogen or $C_1-C_8$alkyl, $R_{11}$ is hydroxyl, $C_1C_{18}$alkoxy or

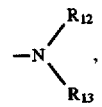

$R_{12}$ and $R_{13}$ independendy of one another are hydrogen or $C_1-C_{18}$alkyl, $R_{14}$ is a direct bond, $C_1C_{18}$alkylene or $C_2-C_{18}$alkylene which is interrupted by oxygen, sulfur or

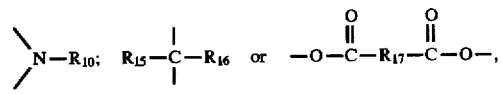

$R_{15}$ and $R_{16}$ independenfiy of one another are hydrogen, $CF_3$, $C_1-C_{12}$alkyl or phenyl, or $R_{15}$ and $R_{16}$, together with the C atom to which they are bonded, form a $C_5C_8$cycloalkylidene ring which is unsubstimted or substituted by 1 to 3 $C_1-C_4$alkyl groups, $R_{17}$ is a direct bond, $C_1C_{18}$alkylene or $C_2-C_{18}$alkylene which is interrupted by oxygen, sulfur or

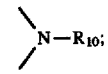

$C_2-C_{18}$alkenylene, $C_2-C_{20}$alkylidene, $C_7C_{20}$phenylalkylidene, $C_5-C_8$cycloalkylene, $C_7C_8$bicycoalcne, phcnyenc which is unsuhsdtuted or substituted by $C_1C_4$alkyl,

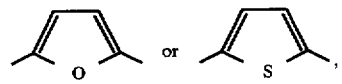

m is 0,1 or 2 and n is 1 or 2.

2. A composition according to claim 1, in which $R_1$, $R_2$, $R_3$, $R_4$, $R_5$, $R_6$, $R_7$ and $R_8$ independently of one another are hydrogen, chlorine $C_1C_{18}$alkyl or $C_2-C_{18}$alkyl which is interrupted by oxygen, sulfur or

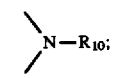

$C_5C_8$cycloalkyl which is unsubstituted or substituted by $CFC_4$alkyl; phenyl which is unsubstituted or substituted by $C_1-C_4$alkyl; $C_7-C_9$phgnylalkyl, hydroxyl, $C_1-C_{18}$alkoxy or $C_3-C_{18}$alkoxy which is interrupted by oxygen, sulfur or

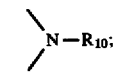

mercapto, $C_1-C_{18}$alkylthio, $C_1-C_{18}$alkanoyloxy or $C_3-C_{18}$alkanoyloxy which is interrupted by oxygen, sulfur or

$C_3$–$C_{18}$alkenoyloxy, benzoyloxy or benzoyloxy which is substituted by $C_1$–$C_8$alkyl; nitro, cyano, —$(CH_2)_m$COR$_{11}$ or

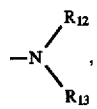

and furthermore the radicals $R_1$ and $R_2$, $R_2$ and $R_3$, $R_3$ and $R_4$, $R_5$ and $R_6$, $R_6$ and $R_7$ or $R_7$ and $R_8$, together with the carbon atoms to which they are bonded, form a benzo ring, or the same pairs of radicals together are —O(CH$_2$)$_n$O—, with the condition that at least one of the radicals $R_1$, $R_2$, $R_3$ or $R_4$ and at least one of the radicals $R_5$, $R_6$, $R_7$ or $R_8$ is hydrogen, $R_1$ is additionally a radical of the formula II, $R_2$ is additionally a radical of the formula III, $R_3$ is additionally a radical of the formula IV and $R_4$ is additionally a radical of the formula V, and in which at the same time only one radical of the formula II, III, IV or V occurs in the compound of the formula I

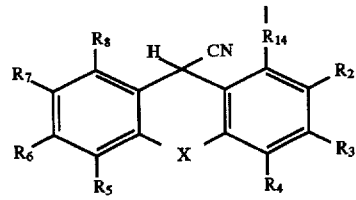 (II)

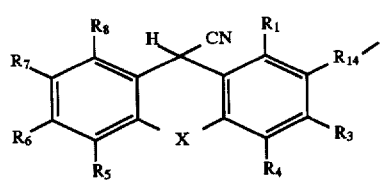 (III)

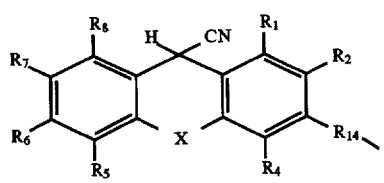 (IV)

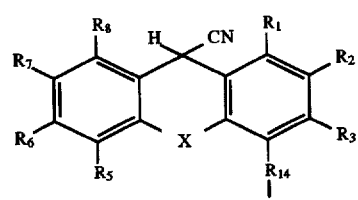 (V)

$R_{11}$ is hydroxyl, $C_1$–$C_{12}$alkoxy or

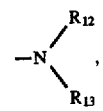

$R_{12}$ and $R_{13}$ independendy of one another are hydrogen or $C_1$–$C_{12}$alkyl, $R_{14}$ is a direct bond, $C_1$C$_{12}$alkylene or $C_2$–$C_{12}$alkylene which is interrupted by oxygen, sulfur or

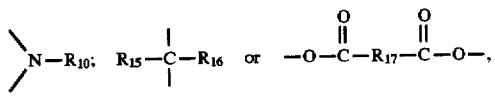

$R_{15}$ and $R_{16}$ independendy of one another are hydrogen, $C_1$–$C_8$alkyl or phenyl, or $R_{15}$ and $R_{16}$, together with the C atom to which they are bonded, form a $C_5$C$_7$cycloalkylidene ring which is unsubstituted or substituted by 1 to 3 $C_1$–$C_4$alkyl groups, and $R_{17}$ is a direct bond, $C_1$–$C_{12}$alkylene or $C_2$–$C_{12}$alkylene which is interrupted by oxygen, sulfur or

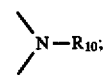

$C_2$–$C_{12}$alkenylene, $C_2$–$C_{16}$alkylidene, $C_7$–$C_{12}$phenylalkylidene, $C_5$C$_7$hdcycloalkylene, phenylene which is unsubsdtuted or substituted by $C_1$–$C_4$alkyl or

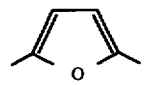

3. A composition according to claim 1, in which $R_5$, $R_6$, $R_7$ and $R_8$ are hydrogen.

4. A composition according to claim 1, in which X is oxygen or sulfur.

5. A composition according to claim 1, in which $R_1$, $R_2$, $R_3$ and $R_4$ independently of one another are hydrogen, chlorine, $C_1$–$C_{18}$alkyl or $C_2$–$C_{18}$alkyl which is interrupted by oxygen; $C_5$C$_8$cycloalkyl, phenyl, $C_7$–$C_9$phenylalkyl, hydroxyl, $C_1$–$C_{18}$alkoxy or $C_3$–$C_{18}$alkoxy which is interrupted by oxygen; $C_1$C$_{18}$alkylthio, $C_1$C$_{18}$alkanoyloxy or $C_3$C$_{18}$alkanoyloxy which is interrupted by oxygen; $C_3$C$_{18}$alkenoyloxy, benzoyloxy, cyano, —$(CH_2)_m$COR$_{11}$ or

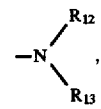

with the condition that at least one of the radicals $R_1$, $R_2$, $R_3$ or $R_4$ is hydrogen, $R_2$ is additionally a radical of the formula III and $R_4$ is additionally a radical of the formula V, and in which at the same time only one radical of the formula III or V occurs in the compound of the formula I

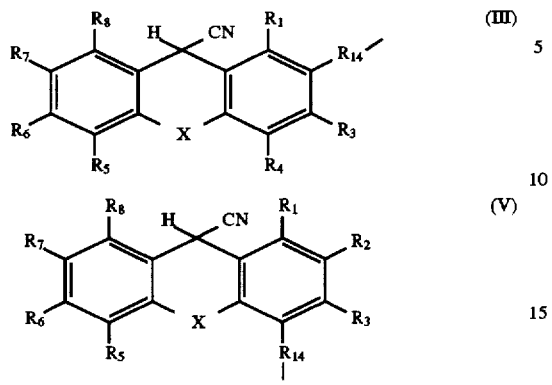

$R_5$, $R_6$, $R_7$ and $R_8$ independently of one another are hydrogen, chlorine, $C_1$–$C_{18}$alkyl, $C_5$$C_8$cycloalkyl, phenyl, benzyl, hydroxyl, $C_1$$C_{18}$alkoxy, $C_1$–$C_{18}$alkylthio, $C_1$$C_{18}$alkanoyloxy, $C_3$$C_{18}$alkenoyloxy, benzoyloxy, cyano, —$(CH_2)_m$$COR_{11}$ or

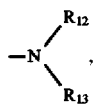

with the condition that at least one of the radicals $R_5$, $R_6$, $R_7$ or $R_8$ is hydrogen, $R_{11}$ is $C_1$$C_{12}$alkoxy or

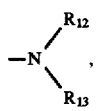

$R_{12}$ and $R_{13}$ independently of one another are hydrogen or $C_1$$C_{18}$alkyl, $R_{14}$ is $C_1$$C_{18}$alkylene or $C_2$–$C_{12}$alkylene which is interrupted by oxygen;

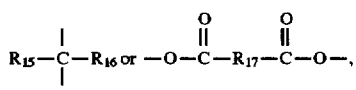

or $R_{15}$ and $R_{16}$ independently of one another are hydrogen, $C_1$$C_{18}$alkyl or phenyl, or $R_5$ and $R_{16}$, together with the C atom to which they are bonded, form a $C_5$–$C_7$cycloalkylidene ring and $R_{17}$ is $C_1$$C_8$alkylene or $C_2$–$C_8$alkylene which is interrupted by oxygen; $C_2$–$C_8$alkenylene, $C_2$–$C_8$alkylidene, $C_5$$C_7$cycloalkylene or phenylene.

6. A composition according to claim 1, in which $R_1$, $R_2$, $R_3$ and $R_4$ independently of one another are hydrogen, $C_1$–$C_8$alkyl, $C_5$–$C_8$cycloalkyl, phenyl, $C_7$–$C_9$phenylalkyl, hydroxyl, $C_1$–$C_{18}$alkoxy, $C_1$–$C_{18}$alkanoyloxy, $C_3$$C_{18}$alkenoyloxy, benzoyloxy, cyano or —$(CH_2)_m COR_{11}$, with the condition that at least one of the radicals $R_1$, $R_2$, $R_3$ or $R_4$ is hydrogen, $R_2$ is additionally a radical of the formula III and $R_4$ is additionally a radical of the formula V, and in which at the same time only one radical of the formula III or V occurs in the compound of the formula I

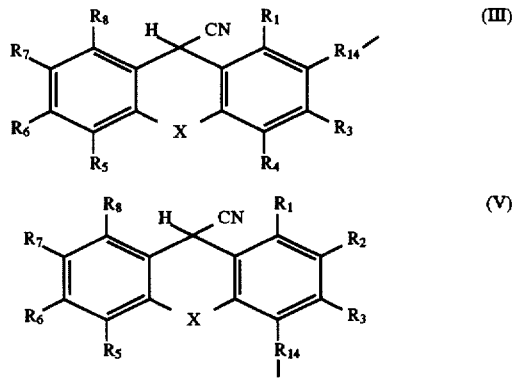

$R_5$, $R_6$, $R_7$ and $R_8$ independendy of one another are hydrogen, chlorine, $C_1$–$C_{18}$alkyl, $C_5$–$C_8$cycloalkyl, phenyl, benzyl or cyano, with the condition that at least one of the radicals $R_5$, $R_6$, $R_7$ or $R_8$ is hydrogen, $R_{11}$ is $C_1$$C_{12}$alkoxy, $R_4$ is $C_1C_8$alkylene, $C_2C_{12}$alkylene which is interrupted by oxygen or

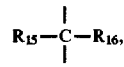

$R_{15}$ and $R_{16}$ independendy of one another are hydrogen, $C_1$$C_8$alkyl or phenyl, or $R_{15}$ and $R_{16}$, together with the C atom to which they are bonded, form a $C_5$$C_7$cycloalkylidene ring, X is oxygen or sulfur, and m is 0 or 1.

7. A composition according to claim 1, in which $R_1$, $R_2$, $R_3$ and $R_4$ independently of one another are hydrogen, $C_1$–$C_{12}$alkyl, cyclohexyl, $C_7$–$C_9$phenylalkyl, hydroxyl, $C_1$–$C_2$alkoxy, $C_1$–$C_{12}$alkanoyloxy or —$(CH_2)_mCOR_{11}$, with the condition that at least one of the radicals $R_1$, $R_2$, $R_3$ or $R_4$ is hydrogen, $R_5$, $R_6$, $R_7$ and $R_8$ independently of one another are hydrogen, chlorine, $C_1C_8$alkyl or cyclohexyl, with the condition that at least one of the radicals $R_5$, $R_6$, $R_7$ or $R_8$ is hydrogen, $R_{11}$ is $C_1$$C_{12}$alkoxy, X is oxygen or sulfur, and m is 0 or 1.

8. A composition according to claim 1, in which $R_1$ is hydrogen, hydroxyl, or $C_1$–$C_{12}$alkanoyloxy, $R_2$ is hydrogen, $C_1$–$C_{12}$alkyl, $C_7$$C_9$phenylalkyl, $C_1$–$C_3$alkoxy or —$(CH_2)_mCOR_{11}$, $R_3$ is hydrogen, hydroxyl or $C_1$–$C_{12}$alkanoyloxy, $R_4$ is hydrogen, $C_1$–$C_4$alkyl or cyclohexyl, with the condition that at least one of the radicals $R_1$, $R_2$, $R_3$ or $R_4$ is hydrogen, $R_5$, $R_6$, $R_7$ and $R_8$ are hydrogen, $R_{11}$ is $C_1$–$C_{12}$alkoxy, X is oxygen or sulfur, and m is 0 or 1.

9. A composition according to claim 1, additionally comprising, in addition to components (a) and (b) further additives.

10. A composition according to claim 9, comprising phenolic antioxidants, light stabilizers and/or processing stabilizers as further additives.

11. A composition according to claim 9, comprising at least one compound of the organic phosphite or phosphonite type as a further additive.

12. A composition according to claim 1, comprising natural, semi-synthetic or synthetic polymers as component a).

13. A composition according to claim 1, comprising thermoplastic polymers, tackifiers or adhesives as component (a).

14. A composition according to claim 1, comprising a polyolefin as component (a).

15. A composition according to claim 1, comprising polyethylene or polypropylene as component (a).

16. A composition according to claim 1, in which component b) is present in an amount of 0.0005 to 5%, based on the weight of component a).

* * * * *

UNITED STATES PATENT AND TRADEMARK OFFICE
CERTIFICATE OF CORRECTION

PATENT NO. : 5,710,198
DATED : January 20, 1998
INVENTOR(S) : RITA PITTELOUD

It is certified that error appears in the above-identified patent and that said Letters Patent is hereby corrected as shown below:

In claim 1, column 44 insert between lines 40 and 41 the following:

-- X is oxygen or sulfur, --

Signed and Sealed this

Thirtieth Day of June, 1998

Attest:

BRUCE LEHMAN

Attesting Officer    Commissioner of Patents and Trademarks